United States Patent
Roussel et al.

(10) Patent No.: US 7,906,541 B2
(45) Date of Patent: Mar. 15, 2011

(54) PROCESS TO PREPARE NEW SUBSTITUTED 1H-BENZO[D]IMIDAZOL-2(3H)-ONES, NEW INTERMEDIATES AND THEIR USE AS BACE 1 INHIBITORS

(75) Inventors: Christian Roussel, Aubagne (FR); Frederico Andreoli, Modena (IT); Nicolas Daniel Pierre Vanthuyne, Marseilles (FR)

(73) Assignee: Universite Paul Cezanne-Aix Marseille III, Cedex (FR)

( * ) Notice: Subject to any disclaimer, the term of this patent is extended or adjusted under 35 U.S.C. 154(b) by 0 days.

(21) Appl. No.: 12/329,739

(22) Filed: Dec. 8, 2008

(65) Prior Publication Data
US 2010/0120880 A1    May 13, 2010

(30) Foreign Application Priority Data
Nov. 7, 2008    (EP) .................................... 08291046

(51) Int. Cl.
A61K 31/4184    (2006.01)
C07D 235/26    (2006.01)
(52) U.S. Cl. .................................... 514/387; 548/306.4
(58) Field of Classification Search ................ 514/387; 548/306.4
See application file for complete search history.

(56) References Cited

U.S. PATENT DOCUMENTS
2006/0183790 A1    8/2006    Cole et al.

FOREIGN PATENT DOCUMENTS
| WO | 2008013925 A2 | 1/2008 |
| WO | 2008032164 A2 | 3/2008 |
| WO | 2008051533 A2 | 5/2008 |
| WO | 2008061968 A1 | 5/2008 |
| WO | 2008065508 A1 | 6/2008 |
| WO | 2008070150 A1 | 6/2008 |
| WO | 2008070264 A1 | 6/2008 |
| WO | 2008070268 A2 | 6/2008 |
| WO | 2008115552 A1 | 9/2008 |

OTHER PUBLICATIONS

Duarte, CD et al. Privileged Structures: A Useful Concept for the Rational Design of New Lead Drug Candidates. Mini-Reviews in Medicinal Chemistry. 2007. Benthan Science Publishers. vol. 7. pp. 1108-1119.

Kubinyi, Hugo. Privileged Structures and Analogue-Based Drug Discovery. In Analogue-Based Drug Discovery. 2006. pp. 53-68.

Zou, B et al. Cascade Coupling/Cyclization Process to N-Substituted 1,3-Dihydrobenzimidazol-2-ones. Organic Letters. 2007. American Chemical Society. vol. 9. No. 21. pp. 4291-4294.

Xu, X et al. Microwave-assisted traceless synthesis of benzimidazolones. Tetrahedron Letters 48 (2007). 2006. Elsevier. pp. 129-132.

McLaughlin, M et al. Efficient Access to Cyclic Ureas via Pd-Catalyzed Cyclization. Organic Letters. 2006. American Chemical Society. vol. 8. No. 15. pp. 3311-3314.

Kuethe, JT et al. Rearrangement of spiro-benzimidazolines: preparation of N-alkenyl- and N-alkyl-benzinnidazol-2-ones. Tetrahedron 63 (2007). 2007. Elsevier. pp. 11489-11502.

Roussel, C et al. New Route to 3-Alkylthiazolo[3,2-a]benzimidazole Derivatives. Molecules. 2005. MDPI. vol. 10. pp. 327-333.

Edwards, PD et al. Application of Fragment-Based Lead Generation to the Discovery of Novel, Cyclic Amidine β-Secretase Inhibitors with Nanomolar Potency, Cellular Activity, and High Ligand Efficiency. J. Med. Chem. 2007. American Chemical Society. vol. 50. pp. 5912-5925.

European Search Report, EP 08 29 1046 dated Mar. 24, 2009.

*Primary Examiner* — Kamal A Saeed
*Assistant Examiner* — Kristin Bianchi
(74) *Attorney, Agent, or Firm* — Lesley S. Craig

(57) ABSTRACT

The invention relates to a new process leading to new substituted 1H-benzo[d]imidazol-2(3H)-ones of formula III and III', to pharmaceutical compositions comprising them and to their use as therapeutic agents, particularly as BACE 1 inhibitors in the treatment of Alzheimer disease.

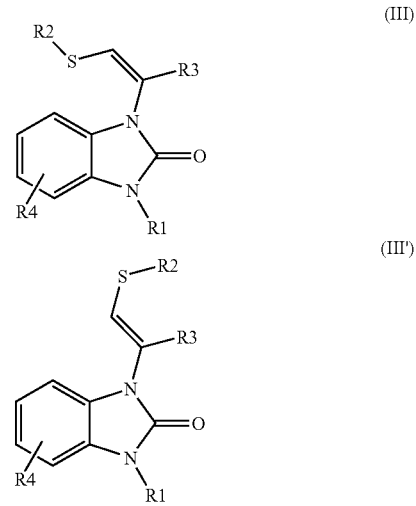

21 Claims, No Drawings

PROCESS TO PREPARE NEW SUBSTITUTED 1H-BENZO[D]IMIDAZOL-2(3H)-ONES, NEW INTERMEDIATES AND THEIR USE AS BACE 1 INHIBITORS

FIELD OF THE INVENTION

The invention relates to a new process leading to new substituted 1H-benzo[d]imidazol-2(3H)-ones, to pharmaceutical compositions comprising them and to their use as therapeutic agents, particularly as BACE 1 inhibitors in the treatment of Alzheimer disease.

BACKGROUND OF THE INVENTION

Substituted 1H-benzo[d]imidazol-2(3H)-ones (A) are heterocyclic compounds which belong to the happy few class of "privileged" structures.

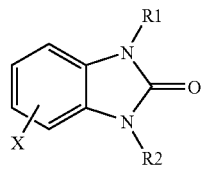

Privileged structures are defined as "molecular frameworks which are able of providing useful ligands for more than one type of receptor or enzyme target by judicious structural modifications". (Duarte, Carolina D.; Barreiro, Eliezer J.; Fraga, Carlos A. M., Mini-Reviews in Medicinal Chemistry (2007), 7(11), 1108-1119. "*Privileged structures and analogue-based drug discovery*" Kubinyi, Hugo. In Analogue-Based Drug Discovery (2006), 53-68. Editor(s): Fischer, Janos; Ganellin, C. Robin. Wiley-VCH Verlag GmbH & Co. KGaA, Weinheim, Germany).

The status of privileged structure results from the outstanding number of application of this framework in various type of receptors or enzyme targets. More than 8000 differently substituted 1H-benzo[d]imidazol-2(3H)-ones have been associated with biological application in the chemical and patent literature according to the Chemical Abstracts.

The interest in new derivatives and new applications is still vivid as exemplified in recent patent application such as WO 2008065508 for treatment of obesity, WO 2007-US80831 describing the use of domperidone for reducing analgesics adverse effect, WO 2008070150 for treating hyper-proliferative disorders and diseases associated with angiogenesis, WO 2008070264 describing a nasal spray composition comprising antihistamine, anti-inflammatory agent and decongestant for treating rhinitis and/or sinusitis, WO 2008061968 for benzimidazolone derivatives displaying affinity for the 5-HT2B-receptor in the treatment of pulmonary arterial hypertension, WO 2008051533 for the preparation of benzimidazole derivatives as CRF receptor antagonists, WO 2008013925 for fungicidal azocyclic amides, WO 2008032164 for benzimidazolone derivatives and their preparation, pharmaceutical compositions and use in the treatment of CB1 and CB2 receptor mediated diseases.

The status of privileged structure and the need of the optimization of the substitution pattern impelled the development of libraries of benzimidazolones in several pharmaceutical companies.

The preparation of libraries of 1H-benzo[d]imidazol-2 (3H)-one derivatives rests on the discovery of highly efficient and regioselective synthetic methods for the preparation of the 1H-benzo[d]imidazol-2(3H)-one differently substituted on the N1 and N3 nitrogen atom. (Zou, B.; Yuan, Q.; Ma, D. Organic Lett., 2007, 9(21), 4291-4294. Xu, X-J.; Zong, Y-X. Tetrahedron Lett. 2007, 48, 129-132. McLaughlin, M.; Palucki, M.; Davies, I. W. Org. Lett. 2006, 8, 3311-3314 and reference therein).

Among the thousands of N1,N3 disubstituted 1H-benzo[d] imidazol-2(3H)-ones, those presenting an N-alkenyl substituent such as compound of formula (B), occupy a special position since the alkenyl group can be considered as a protecting group which can be hydrolyzed to yield regioselectively R2-substituted 1H-benzo[d]imidazol-2(3H)-ones.

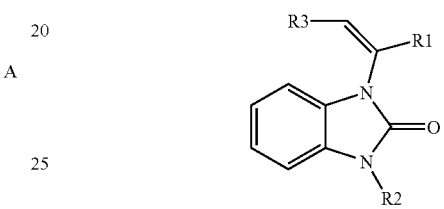

The synthesis of these compounds B starts from the 1,2-diaminobenzene which is reacted on a beta ketoester according to Scheme A.

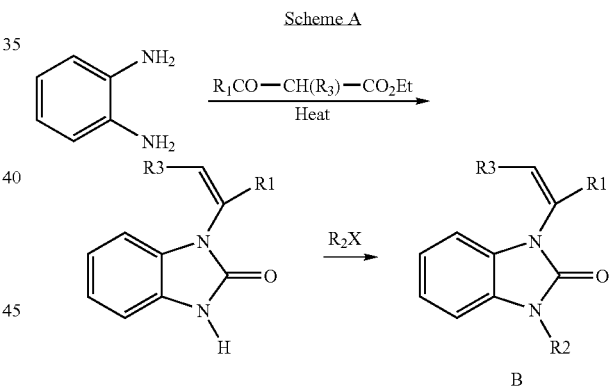

In this process several by-products have been identified which decrease severely the reaction yield. (Kuethe, J. T.; Varon, J.; Childers, K. G. Tetrahedron 2007, 63, 11489-11502 and references therein). Recently, spirobenzimidazolines were shown to rearrange in basic medium and triphosgene to yield N-alkenyl-benzimidazolinones (X=O, S, NR) (Kuethe, J. T.; Varon, J.; Childers, K. G. Tetrahedron 2007, 63, 11489-11502).

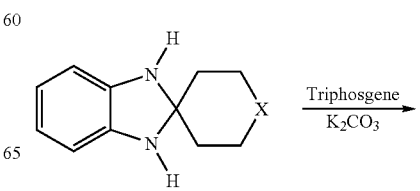

-continued

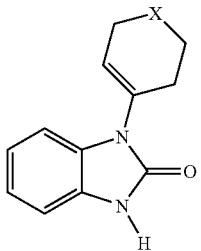

SUMMARY OF THE INVENTION

The present invention is related to a new process for preparing compounds of formula III and III'

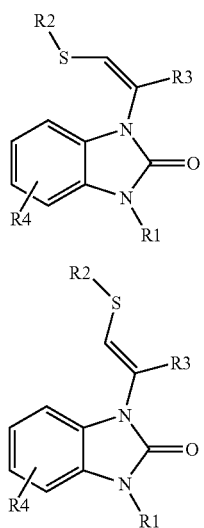

The process comprises the step of treatment of a substituted thiazolo[3,2-a]benzimidazolium quaternary salt (II)

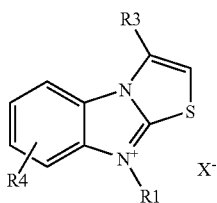

with an alkoxide $R_2OM$ where M is a sodium or a potassium cation in the corresponding alcohol and wherein $R_1$, $R_2$, $R_3$, $R_4$ have the meaning as defined below.

$R_1$ and $R_2$ being identical or different represent:
a linear or branched $C_1$-$C_{10}$ alkyl group optionally functionalized by
  one or more linear or cyclic $C_1$-$C_8$ O-alkyl or S-alkyl groups, and/or
  O-aryl having from 6 to 10 carbon atoms optionally substituted by one or more group selected from the group consisting of halogens $NO_2$, CN, $CF_3$, $CCl_3$, $CO_2R_i$;
an arylalkyl group composed of an aromatic ring having from 6 to 10 carbon atoms optionally substituted by one or more group selected from the group consisting of linear and branched $C_1$-$C_{10}$ alkyl, $C_1$-$C_4$ alkoxy, $C_6$-$C_{10}$-aryloxy groups, OH, $CO_2R_i$, linked to
the sulfur heteroatom or nitrogen by a $C_1$-$C_4$ alkyl group;
A heterocyclic group, linked to the nitrogen or the sulfur heteroatom by an alkyl $C_1$-$C_4$ chain, optionally functionalized by one or several substituents selected from the series consisting of $NO_2$, CN, $CF_3$, $CCl_3$ halogen (F, Cl, Br, I), OH, $CO_2R_i$.

$R_3$ represents:
a linear or branched $C_1$-$C_{10}$ alkyl group optionally functionalized by $C_1$-$C_4$ alkoxy, $C_6$-$C_{10}$-aryloxy groups or halogen,
a $C_6$-$C_{10}$ aryl or heterocyclic group optionally functionalized by one or several substituents selected from the series consisting of $NO_2$, CN, $CF_3$, $CCl_3$, halogen (F, Cl, Br, I), linear and branched $C_1$-$C_{10}$ alkyl, $C_1$-$C_4$ alkoxy, $C_6$-$C_{10}$-aryloxy groups, OH, $CO_2R_i$.

R4 which can occupy any of the four positions of the aromatic ring and is selected from the group consisting of hydrogen, $NO_2$, CN, $CF_3$, $CCl_3$, halogen (F, Cl, Br, or I), linear and branched $C_1$-$C_{10}$ alkyl, $C_1$-$C_4$ alkoxy, $C_6$-$C_{10}$-aryloxy groups, OH, $CO_2R_i$ or $R_4$ can be composed of one to four identical or different substituents selected from the group consisting of $NO_2$, CN, $CF_3$, $CCl_3$, halogen (F, Cl, Br, I), linear and branched $C_1$-$C_{10}$ alkyl, $C_1$-$C_4$ alkoxy, $C_6$-$C_{10}$-aryloxy groups, OH, $CO_2R_i$.

and $R_i$ is a $C_1$-$C_4$ alkyl group.

In a preferred embodiment of the process of the invention, compounds of formula III or III' are prepared wherein $R_2$ is Me, $R_3$ is Me, $R_4$ is H and $R_1$ is Me, Et, $C_3$-$C_{10}$ n-alkyl group, —$CH_2CH_2$Oalkyl, —$CH_2CH_2OCF_3$, —$CH_2CH_2$(OCH$_2$CH$_2$)$_n$—OH, —$CH_2CH_2$—(OCH$_2$CH$_2$)$_n$OMe, —$CH_2CH_2$—(OCH$_2$CH$_2$)$_n$OPh, —$CH_2CH_2$—(SCH$_2$CH$_2$)$_n$—OH—$CH_2CH_2$(SCH$_2$CH$_2$)$_n$SMe, —$CH_2CH_2$(SCH$_2$CH$_2$)$_n$ SPh, —$CH_2CH(OMe)_2$, —$CH_2CH(SMe)_2$, —$CH_2CH(O(CH_2)_nO)$, —$CH_2CH(S(CH_2)_nS)$, —$CH_2CH_2$(OCH$_2$CH$_2$)$_n$OPhR, —$CH_2CH_2$(OCH$_2$CH$_2$)$_n$OPhRR', and wherein R, R' identical or different are selected from the group consisting of o, m, p- $C_1$-$C_4$ alkyl, F, Cl, Br, I, $NO_2$, $CF_3$, $CCl_3$, CN, $CO_2Me$ and wherein n is 0 to 4.

In a preferred embodiment of the process of the invention, compounds of formula III or III' are prepared wherein $R_2$ is Me or benzyl, $R_3$ is Me, $R_4$ is H and $R_1$ is benzyl, $CH_2PhR$, $CH_2PhRR'$ wherein R, R' identical or different are selected from the group consisting of o, m, p- $C_1$-$C_4$ alkyl, F, Cl, Br, I, $NO_2$, $CF_3$, $CCl_3$, CN, $CO_2Me$, or $R_1$ is $CH_2Ar$ in which Ar is 2-naphthalenyl, 1-naphthalenyl optionally functionalized by F, Cl, Br, I, $NO_2$, $CF_3$, $CCl_3$, CN or $CO_2Me$.

In a preferred embodiment of the process of the invention, compounds of formula III or III' are prepared wherein $R_1$ is Me, $R_3$ is Me, $R_4$ is H and $R_2$ is benzyl, $CH_2PhR$, $CH_2PhRR'$ wherein R, R' identical or different are selected from the group consisting of o, m, p- $C_1$-$C_4$ alkyl, F, Cl, Br, I, $NO_2$, $CF_3$, $CCl_3$, CN, $CO_2Me$, or $R_2$ is $CH_2$-Heterocycle in which Heterocycle is 2-pyridyl, 3-pyridyl, 4-pyridyl, 2-thienyl, 3-thienyl, 2-furanyl, 3-furanyl, 2-thiazolyl, 2-benzothiazolyl, 2-imidazolyl, furfuryl, or $R_2$ is $CH_2Ar$ in which Ar is 2-naphthalenyl, 1-naphthalenyl optionally functionalized by F, Cl, Br, I, $NO_2$, $CF_3$, $CCl_3$, CN or $CO_2Me$.

In a preferred embodiment of the process of the invention, compounds of formula III or III' are prepared wherein $R_1$ is Benzyl, $R_3$ is Me, $R_4$ is H and $R_2$ is benzyl, $CH_2PhR$, $CH_2PhRR'$ wherein R, R' identical or different are selected from the group consisting of o, m, p- $C_1$-$C_4$ alkyl, F, Cl, Br, I, $NO_2$, $CF_3$, $CCl_3$, CN, $CO_2Me$, or $R_2$ is $CH_2$-Heterocycle in which Heterocycle is 2-pyridyl, 3-pyridyl, 4-pyridyl, 2-thienyl, 3-thienyl, 2-furanyl, 3-furanyl, 2-thiazolyl, 2-benzothiazolyl, 2-imidazolyl, furfuryl.

In a preferred embodiment of the process of the invention, compounds of formula III or III' are prepared wherein $R_1$ is Me, $R_3$ is Me, $R_4$ is H and $R_2$ is Me, Et, $C_3$-$C_{10}$ n-alkyl group, —$CH_2CH_2O$alkyl, —$CH_2CH_2OCF_3$, —$CH_2CH_2(OCH_2CH_2)_n$—OH, —$CH_2CH_2$—$(OCH_2CH_2)_n$OMe, —$CH_2CH_2$—$(OCH_2CH_2)_n$OPh, —$CH_2CH_2$—$(SCH_2CH_2)_n$—OH, —$CH_2CH_2(SCH_2CH_2)_n$SMe, —$CH_2CH_2(SCH_2CH_2)_n$SPh, —$CH_2CH(OMe)_2$, —$CH_2CH(SMe)_2$, —$CH_2CH(O(CH_2)_nO)$, —$CH_2CH(S(CH_2)_nS)$, —$CH_2CH_2(OCH_2CH_2)_n$OPhR, —$CH_2CH_2(OCH_2CH_2)_n$OPhRR', and wherein R R' identical or different are selected from the group consisting of o, m, p- $C_1$-$C_4$ alkyl, F, Cl, Br, I, $NO_2$, $CF_3$, $CCl_3$, CN, $CO_2Me$ and wherein n is 0 to 4.

In a preferred embodiment of the process of the invention, compounds of formula III or III' are prepared wherein $R_1$ is Me or benzyl, $R_2$ is Me or benzyl, $R_3$ is Me, $R_4$ in position 4 or 5 is $CF_3$, F, Cl, Br, $NO_2$, CN, Me, MeO or $R_4$ is 4,5-dichloro, 4,5-dimethyl, 4,5-dimethoxy.

According to the invention, in the process for selectively obtaining compound (III) the step of treatment is conducted at a temperature below 60° C., preferably from about 18 to about 35° C.

According to the invention, in the process for selectively obtaining a mixture of compound (III) and (III'), the step of treatment is conducted at a temperature above 70° C., preferably above 100° C.

Another object of the invention is the process for obtaining compound (IV)

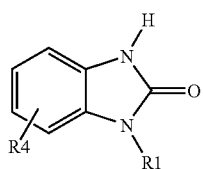

(IV)

by hydrolysis conducted in a mixture MeOH/Water and catalyzed by a protonic acid of compound of formula (III) or (III') as defined above.

Another object of the invention is a compound of formula (III) or (III') or a mixture thereof,

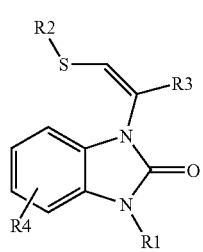

(III)

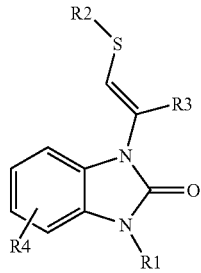

(III')

$R_1$, $R_2$, $R_3$, $R_4$ being as defined above, or a pharmaceutical acceptable salt thereof.

Another object of the invention is a compound selected from the group consisting of:

1-methyl-3-[(1Z)-1-(methylsulfanyl)prop-1-en-2-yl]-1,3-dihydro-2H-benzimidazol-2-one;

1-benzyl-3-[(1Z)-1-(methylsulfanyl)prop-1-en-2-yl]-1,3-dihydro-2H-benzimidazol-2-one);

1-[(1Z)-1-(benzylsulfanyl)prop-1-en-2-yl]-3-methyl-1,3-dihydro-2H-benzimidazol-2-one;

1-[(1E)-1-(benzyl sulfanyl)prop-1-en-2-yl]-3-methyl-1,3-dihydro-2H-benzimidazol-2-one;

1-benzyl-3-[(1Z)-1-(benzyl sulfanyl)prop-1-en-2-yl]-1,3-dihydro-2H-benzimidazol-2-one;

1-benzyl-3-[(1E)-1-(benzylsulfanyl)prop-1-en-2-yl]-1,3-dihydro-2H-benzimidazol-2-one;

1-ethyl-3-[(1Z)-1-(methylsulfanyl)prop-1-en-2-yl]-1,3-dihydro-2H-benzimidazol-2-one;

1-[3,5-bis(trifluoromethyl)benzyl]-3-[(12)-1-(methylsulfanyl)prop-1-en-2-yl]-1,3-dihydro-2H-benzimidazol-2-one;

1-heptyl-3-[(1Z)-1-(methylsulfanyl)prop-1-en-2-yl]-1,3-dihydro-2H-benzimidazol-2-one;

1-[(1Z)-1-(methylsulfanyl)prop-1-en-2-yl]-3-(4-nitrobenzyl)-1,3-dihydro-2H-benzimidazol-2-one;

1-methyl-3-[(1Z)-1-(methylsulfanyl)prop-1-en-2-yl]-5-(trifluoromethyl)-1,3-dihydro-2H-benzimidazol-2-one;

5-fluoro-3-methyl-1-[(1Z)-1-(methylsulfanyl)prop-1-en-2-yl]-1,3-dihydro-2H-benzimidazol-2-one;

or a pharmaceutical acceptable salt thereof.

Another object of the invention is a pharmaceutical composition comprising at least one compound of formula III or III' as defined above and a pharmacologically acceptable carrier.

Another object of the invention is a pharmaceutical composition comprising at least one compound of formula III or III' as defined above for its use as BACE 1 inhibitor.

Another object of the invention is the use of an effective amount of a compound of formula III or III' as defined above for the manufacture of a drug for the treatment of Alzheimer diseases in a human or other animal subject, wherein said treatment comprises administering said drug to said subject.

DETAILED DESCRIPTION

The new process for preparing compounds of formula III and III' is detailed in the scheme 1 below:

Scheme 1

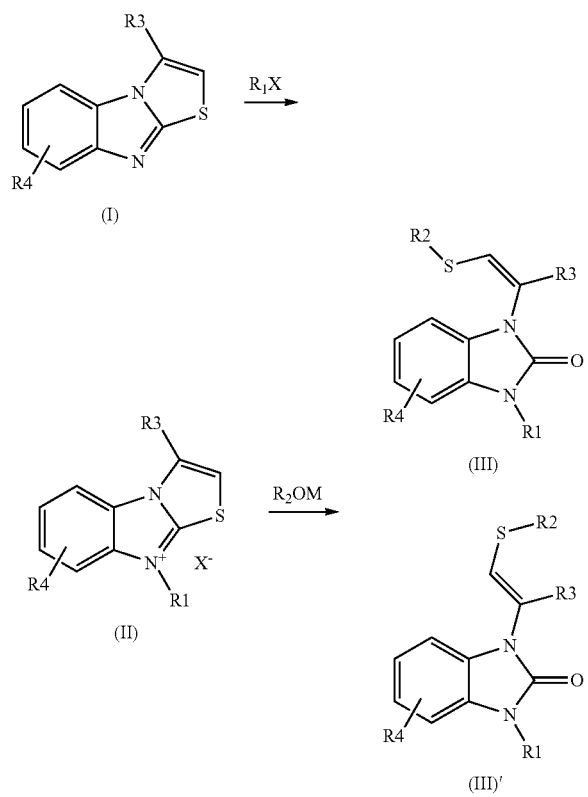

Scheme 2

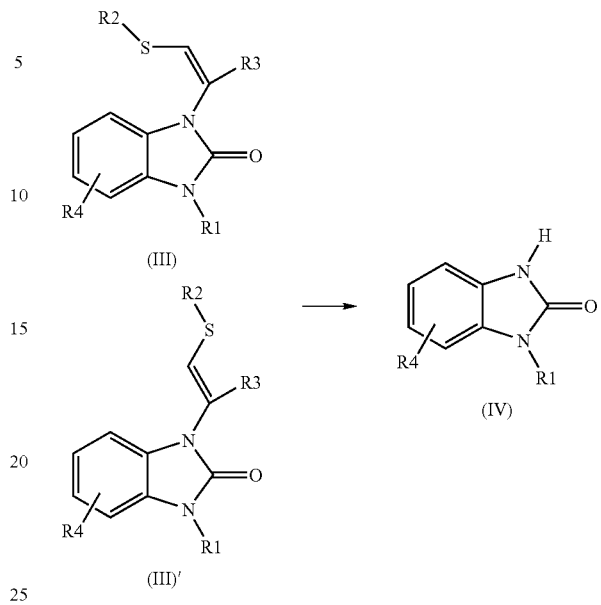

R₂OM can be prepared in situ from the corresponding hydroxide and R₂OH or in a preferred manner R₂OM is prepared independently according to classical methods.

In an unexpected manner the alkoxide anion $R_2O^-$ is broken up during the process to yield the $R_2$ substituent on sulfur atom and the oxygen of the 1H-benzo[d]imidazol-2(3H)-one.

Thus the molecular diversity of the $R_2$ substituent is brought about by the alkoxide.

Compounds III or III' can be obtained as single isomer or mixture of them depending on the operating conditions. More precisely operating temperature up to 60° C., preferably from 18° C. to 35° C. yielded the Z isomer alone (compound of formula III), while a mixture of the Z/E isomers is obtained for higher temperatures, namely for temperatures above 70° C., preferably above 100° C. Then the E isomer alone (compound of formula III') is obtained by liquid chromatography.

Substituted thiazolo[3,2-a]benzimidazolium quaternary salts (II) are prepared in high yield by quaternization of the parent substituted thiazolo[3,2-a]benzimidazole (I) with $R_1X$ according to known processes with or without solvent. This step brings the molecular diversity of the $R_1$ group in a very selective and efficient manner.

Substituted thiazolo[3,2-a]benzimidazoles (I) which carry the structural diversity for the substituents $R_4$ and $R_3$ in the final products III and III' are easily prepared according to known procedures. (Roussel, C.; Andreoli, F.; Roman, M.; Hristova, M.; Vanthuyne, N. *Molecules* 2005, 10, 327-333 and references therein)

In another embodiment, the invention concerns the process for the preparation of compounds of formula IV wherein $R_1$ $R_4$ have the same meaning as defined above by hydrolysis of compound III or compound III' alone or in a mixture of compound III and compound III' according to Scheme 2.

Compounds (IV) are well known compounds which can be regioselectively obtained in high yields according to the process of the invention which consists in a hydrolysis catalyzed by a protonic acid (Broensted acid) in a mixture methanol/water starting from compounds III and/or III'.

The present invention also relates to compounds of formula III and III'

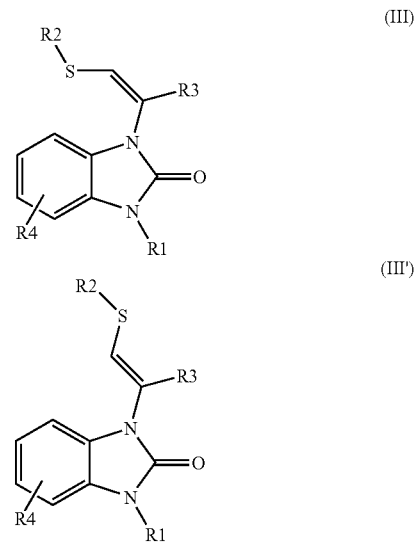

wherein $R_1$, $R_2$, $R_3$, $R_4$ have the same meaning as defined above.

Preferred compounds are those of formula III and III' wherein $R_2$ is Me, $R_3$ is Me, $R_4$ is H and $R_1$ is Me, Et, $C_3$-$C_{10}$ n-alkyl group, —CH₂CH₂Oalkyl, —CH₂CH₂OCF₃, —CH₂CH₂(OCH₂CH₂)$_n$—OH, —CH₂CH₂—(OCH₂CH₂)$_n$OMe, —CH₂CH₂—(OCH₂CH₂)$_n$OPh, —CH₂CH₂—(SCH₂CH₂)$_n$—OH—CH₂CH₂(SCH₂CH₂)$_n$SMe, —CH₂CH₂(SCH₂CH₂)$_n$SPh, —CH₂CH(OMe)₂, —CH₂CH(SMe)₂, —CH₂CH(O(CH₂)$_n$O), —CH₂CH(S(CH₂)$_n$S), —CH$_2$CH$_2$(OCH$_2$CH$_2$)$_n$OPhR, —CH$_2$CH$_2$(OCH$_2$CH$_2$)$_n$OPhRR', and wherein R, R' identical or different are selected from the group consisting of o, m, p- C$_1$-C$_4$ alkyl, F, Cl, Br, I, NO$_2$, CF$_3$, CCl$_3$, CN, CO$_2$Me and wherein n is 0 to 4.

Preferred compounds are those of formula III and III' wherein R$_2$ is Me or benzyl, R$_3$ is Me, R$_4$ is H and R$_1$ is benzyl, CH$_2$PhR, CH$_2$PhRR' wherein R, R' identical or different are selected from the group consisting of o, m, p- C$_1$-C$_4$ alkyl, F, Cl, Br, I, NO$_2$, CF$_3$, CCl$_3$, CN, CO$_2$Me, or R$_1$ is CH$_2$Ar in which Ar is 2-naphthalenyl, 1-naphthalenyl optionally functionalized by F, Cl, Br, I, NO$_2$, CF$_3$, CCl$_3$, CN or CO$_2$Me.

Preferred compounds are those of formula III and III' wherein R$_1$ is Me, R$_3$ is Me, R$_4$ is H and R$_2$ is benzyl, CH$_2$PhR, CH$_2$PhRR' wherein R, R' identical or different are selected from the group consisting of o, m, p- C$_1$-C$_4$ alkyl, F, Cl, Br, I, NO$_2$, CF$_3$, CCl$_3$, CN, CO$_2$Me, or R$_2$ is CH$_2$-Heterocycle in which Heterocycle is 2-pyridyl, 3-pyridyl, 4-pyridyl, 2-thienyl, 3-thienyl, 2-furanyl, 3-furanyl, 2-thiazolyl, 2-benzothiazolyl, 2-imidazolyl, furfuryl, or R$_2$ is CH$_2$Ar in which Ar is 2-naphthalenyl, 1-naphthalenyl optionally functionalized by F, Cl, Br, I, NO$_2$, CF$_3$, CCl$_3$, CN or CO$_2$Me.

Preferred compounds are those of formula III and III' wherein R$_1$ is Benzyl, R$_3$ is Me, R$_4$ is H and R$_2$ is benzyl, CH$_2$PhR, CH$_2$PhRR' wherein R, R' identical or different are selected from the group consisting of o, m, p- C$_1$-C$_4$ alkyl, F, Cl, Br, I, NO$_2$, CF$_3$, CCl$_3$, CN, CO$_2$Me, or R$_2$ is CH$_2$-Heterocycle in which Heterocycle is 2-pyridyl, 3-pyridyl, 4-pyridyl, 2-thienyl, 3-thienyl, 2-furanyl, 3-furanyl, 2-thiazolyl, 2-benzothiazolyl, 2-imidazolyl, furfuryl.

Preferred compounds are those of formula III and III' wherein R$_1$ is Me, R$_3$ is Me, R$_4$ is H and R$_2$ is Me, Et, C$_3$-C$_{10}$ n-alkyl group, —CH$_2$CH$_2$Oalkyl, —CH$_2$CH$_2$OCF$_3$, —CH$_2$CH$_2$(OCH$_2$CH$_2$)$_n$—OH, —CH$_2$CH$_2$—(OCH$_2$CH$_2$)$_n$OMe, —CH$_2$CH$_2$—(OCH$_2$CH$_2$)$_n$OPh, —CH$_2$CH$_2$—(SCH$_2$CH$_2$)$_n$—OH, —CH$_2$CH$_2$(SCH$_2$CH$_2$)$_n$SMe, —CH$_2$CH$_2$(SCH$_2$CH$_2$)$_n$SPh, —CH$_2$CH(OMe)$_2$, —CH$_2$CH(SMe)$_2$, —CH$_2$CH(O(CH$_2$)$_n$O), —CH$_2$CH(S(CH$_2$)$_n$S), —CH$_2$CH$_2$(OCH$_2$CH$_2$)$_n$OPhR, —CH$_2$CH$_2$(OCH$_2$CH$_2$)$_n$OPhRR', and wherein R R' identical or different are selected from the group consisting of o, m, p- C$_1$-C$_4$ alkyl, F, Cl, Br, I, NO$_2$, CF$_3$, CCl$_3$, CN, CO$_2$Me and wherein n is 0 to 4.

Preferred compounds are those of formula III and III' wherein R$_1$ is Me or benzyl, R$_2$ is Me or benzyl, R$_3$ is Me, R$_4$ in position 4 or 5 is CF$_3$, F, Cl, Br, NO$_2$, CN, Me, MeO or R$_4$ is 4,5-dichloro, 4,5-dimethyl, 4,5-dimethoxy.

The most preferred compounds according to the invention are:
1-methyl-3-[(1Z)-1-(methylsulfanyl)prop-1-en-2-yl]-1,3-dihydro-2H-benzimidazol-2-one;
1-benzyl-3-[(1Z)-1-(methylsulfanyl)prop-1-en-2-yl]-1,3-dihydro-2H-benzimidazol-2-one);
1-[(1Z)-1-(benzylsulfanyl)prop-1-en-2-yl]-3-methyl-1,3-dihydro-2H-benzimidazol-2-one;
1-[(1E)-1-(benzyl sulfanyl)prop-1-en-2-yl]-3-methyl-1,3-dihydro-2H-benzimidazol-2-one;
1-benzyl-3-[(1Z)-1-(benzylsulfanyl)prop-1-en-2-yl]-1,3-dihydro-2H-benzimidazol-2-one;
1-benzyl-3-[(1E)-1-(benzyl sulfanyl)prop-1-en-2-yl]-1,3-dihydro-2H-benzimidazol-2-one;
1-ethyl-3-[(1Z)-1-(methylsulfanyl)prop-1-en-2-yl]-1,3-dihydro-2H-benzimidazol-2-one;
1-[3,5-bis(trifluoromethyl)benzyl]-3-[(1Z)-1-(methylsulfanyl)prop-1-en-2-yl]-1,3-dihydro-2H-benzimidazol-2-one;
1-heptyl-3-[(1Z)-1-(methylsulfanyl)prop-1-en-2-yl]-1,3-dihydro-2H-benzimidazol-2-one;
1-[(1Z)-1-(methylsulfanyl)prop-1-en-2-yl]-3-(4-nitrobenzyl)-1,3-dihydro-2H-benzimidazol-2-one;
1-methyl-3-[(1Z)-1-(methylsulfanyl)prop-1-en-2-yl]-5-(trifluoromethyl)-1,3-dihydro-2H-benzimidazol-2-one;
5-fluoro-3-methyl-1-[(1Z)-1-(methylsulfanyl)prop-1-en-2-yl]-1,3-dihydro-2H-benzimidazol-2-one
or a pharmaceutical acceptable salt thereof.

The invention relates to a pharmaceutical composition comprising at least one compound of any one of formula III or III' as an active ingredient in addition with one or more pharmaceutical carrier, diluents or excipients.

The composition may, for example, be presented in a form suitable for oral, rectal, parenteral administration or for nasal inhalation: preferred forms include for example, capsules, tablets, coated tables, ampoules, suppositories and nasal spray. The active ingredient may be incorporated in excipients or carriers conventionally used in pharmaceutical compositions.

The compositions are advantageously formulated in dosage units, each dosage unit being adapted to supply a single dose of the active ingredient. Each dosage unit may conveniently contain from 0.01 mg to 100 mg, preferably from 0.1 to 50 mg.

However, it could be necessary to depart from the cited amounts, depending on the body weight or on the administration route, on the individual response to the medicament, on the type of formulation and on the time, or time range, in which the administration is carried out. Therefore, it can be sufficient, in some cases, to use a lower amount then the cited minimum amount, whereas in other cases the higher range could be exceeded. When administering higher amounts, it would be advisable to subdivide them in repeated administrations during the day. Moreover, the compounds of general formula (III) thereof can also be combined with other, different active substances.

In a specific embodiment, the invention relates to the pharmaceutical composition comprising at least one compound of formula III or III' or a mixture thereof for its use as BACE1 inhibitor. BACE1 is a key enzyme involved in the production of amyloid beta-peptides (Abeta) found in extracellular amyloid plaques of Alzheimer's disease. (J. Med. Chem., 2007, 50, 5912-5925).

The pharmaceutical composition according to the invention may be used in the treatment of Alzheimer disease. <<In vitro>> Biological tests were performed through a well established protocol using a BACE1 FRET assay Kit, Red developed by PanVera corporation Madison Wis. USA and marketed by Sigma-Aldrich. Each test was performed in duplicate.

EXAMPLES

Example 1

Preparation of 1-methyl-3-[(1Z)-1-(methylsulfanyl) prop-1-en-2-yl]-1,3-dihydro-2H-benzimidazol-2-one (III, R1=R2=R3=Me, R4=H)

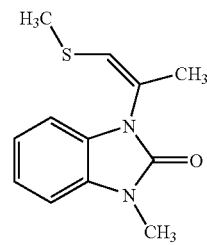

Stage A: Preparation of 3,9-dimethyl[1,3]thiazolo[3,2-a]benzimidazol-9-ium iodide

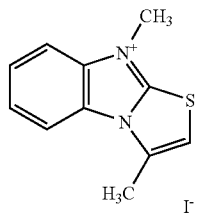

200 mg of 3-methyl[1,3]thiazolo[3,2-a]benzimidazole (prepared according to Roussel, C.; Andreoli, F.; Roman, M.; Hristova, M.; Vanthuyne, N. *Molecules* 2005, 10, 327-333) were solubilised in acetone (3 mL). Then 660 μL (10 eq) of iodomethane were added and the solution stirred at rt. After 24 h, 3,9-dimethyl[1,3]thiazolo[3,2-a]benzimidazol-9-ium iodide was recovered as a white powder (312 mg, 89% yield) by filtration. Mp 210° C. (dec); $^1$H NMR (300 MHz, MeOD) $\delta_H$ 2.95 (3H, d, J=1.2, CH$_3$), 4.16 (3H, s, NCH$_3$), 7.36 (1H, q, J=1.2, H5), 7.65-7.82 (2H, m, Ar), 7.95-8.00 (1H, m, Ar), 8.25-8.29 (1H, m, Ar); $^{13}$C NMR (75 MHz, MeOD) $\delta_C$ 14.21, 33.57, 112.17, 113.56, 114.76, 126.25, 128.32, 128.85, 135.27 138.22, 162.44; HRMS m/z calcd C$_{11}$H$_{11}$N$_2$S [M−I]$^+$: 203.0637; found: 203.0642.

Stage B 350 mg of 3,9-dimethyl[1,3]thiazolo[3,2-a]benzimidazol-9-ium iodide (1.06 mmol) were solubilized in methanol (60 mL), then 230 mg of NaOMe (4 eq) were added and the solution stirred at room temperature. After 48 h the solvent was evaporated, water was added (25 mL) and the mixture extracted with CH$_2$Cl$_2$ (3×25 mL). The organic layer was dried with MgSO$_4$ and evaporated under reduced pressure. The residue was then purified by flash chromatography on silica gel (eluent: CH$_2$Cl$_2$) to afford 1-methyl-3-[(1Z)-1-(methylsulfanyl)prop-1-en-2-yl]-1,3-dihydro-2H-benzimidazol-2-one as a white powder (200 mg, 80% yield). Under other experimental conditions: 100 mg of iodide (III-R3=R1=Me) (0.30 mmol) were solubilised in methanol (20 mL), then 65 mg of NaOMe (4 eq) were added and the solution refluxed for 2 h. Then, the solvent was evaporated, water was added (15 mL) and the mixture extracted with CH$_2$Cl$_2$ (3×15 mL). 1-methyl-3-[(1Z)-1-(methylsulfanyl)prop-1-en-2-yl]-1,3-dihydro-2H-benzimidazol-2-one was recovered (87%, 62 mg) as the sole (Z) isomer.

Mp 66° C. (dec.); $^1$H NMR (300 MHz, CDCl$_3$) $\delta_H$ 2.13 (3H, d, J=1.2, CH$_3$), 2.24 (3H, s, SCH$_3$), 3.43 (3H, s, NCH$_3$), 6.24 (1H, q, J=1.2, H5), 6.85-7.15 (4H, m, arom); $^{13}$C NMR (75 MHz, CDCl$_3$) $\delta_C$ 16.86, 20.34, 27.08, 107.54, 108.88, 121.12, 121.45, 126.60, 127.46, 127.54, 130.29, 152.33; HRMS m/z calcd C$_{12}$H$_{15}$N$_2$OS [M+H]$^+$: 235.0899; found: 235.0901. The (Z) configuration of 1-methyl-3-[(1Z)-1-(methylsulfanyl)prop-1-en-2-yl]-1,3-dihydro-2H-benzimidazol-2-one has been established by NOESY.

Example 2

Preparation of 1-benzyl-3-[(1Z)-1-(methylsulfanyl)prop-1-en-2-yl]-1,3-dihydro-2H-benzimidazol-2-one (III, R1=Benzyl, R2=R3=Me, R4=H)

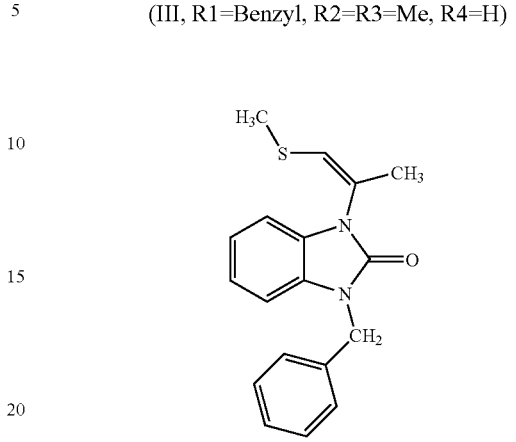

Stage A Preparation of 9-benzyl-3-methyl[1,3]thiazolo[3,2-a]benzimidazol-9-ium chloride.

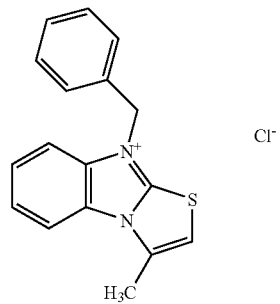

300 mg of 3-methyl[1,3]thiazolo[3,2-a]benzimidazole and 280 μL (1.5 eq) of benzyl chloride were added in acetone (3 mL). The mixture was stirred under reflux and after 48 h 9-benzyl-3-methyl[1,3]thiazolo[3,2-a]benzimidazol-9-ium chloride was recovered as a pale yellow powder (450 mg, 90% yield) by filtration. Mp 227° C. (dec); $^1$H NMR (300 MHz, MeOD) $\delta_H$ 2.92 (3H, d, J=1.2, CH$_3$), 5.77 (2H, s, NCH$_2$), 7.21 (1H, q, J=1.2, H5), 7.45-7.85 (4H, m, arom), 8.05-8.31 (5H, m, arom); $^{13}$C NMR (75 MHz, MeOD) $\delta_C$ 14.07, 51.66, 112.71, 113.87, 114.91, 126.43, 128.46, 128.97, 130.59 (2C), 130.98 (2C), 131.04, 132.58, 134.87, 137.81, 155.75; HRMS m/z calcd C$_{17}$H$_{15}$N$_2$S [M−Cl]$^+$: 279.0950; found: 279.0954.

Stage B: 200 mg of 9-benzyl-3-methyl[1,3]thiazolo[3,2-a]benzimidazol-9-ium chloride (0.635 mmol) were solubilised in methanol (25 mL), then 137 mg of NaOMe (4 eq) were added and the solution stirred at room temperature. After 48 h the solvent was evaporated, water was added (20 mL) and the mixture extracted with CH$_2$Cl$_2$ (3×20 mL). The organic layer was dried with MgSO$_4$ and evaporated under reduced pressure. The residue was then purified by chromatography on silica gel (eluent: CH$_2$Cl$_2$) to afford 1-benzyl-3-[(1Z)-1-(methylsulfanyl)prop-1-en-2-yl]-1,3-dihydro-2H-benzimidazol-2-one as a colourless oil (186 mg, 94% yield). $^1$H NMR (300 MHz, CDCl$_3$) $\delta_H$ 2.18 (3H, d, J=1.1, CH$_3$), 2.26 (3H, s, SCH$_3$), 5.10 (3H, s, NCH$_2$), 6.27 (1H, q, J=1.1, H5), 6.84-7.10 (4H, m, arom), 7.25-7.35 (5H, m, arom); $^{13}$C NMR (75 MHz, CDCl$_3$) $\delta_C$ 16.90, 20.44, 44.79, 108.50, 109.00, 121.24, 121.48, 126.61, 127.37, 127.57 (2C), 127.65, 127.69, 128.69 (2C), 129.45, 136.22, 152.34; HRMS m/z calcd $C_{18}H_{19}N_2OS$ [M+H]$^+$: 311.1212; found: 311.1211.

Example 3

Preparation of 1-[(1Z)-1-(benzylsulfanyl)prop-1-en-2-yl]-3-methyl-1,3-dihydro-2H-benzimidazol-2-one and 1-[(1E)-1-(benzylsulfanyl)prop-1-en-2-yl]-3-methyl-1,3-dihydro-2H-benzimidazol-2-one (III and III', R1=Me, R2=Benzyl, R3=Me, R4=H)

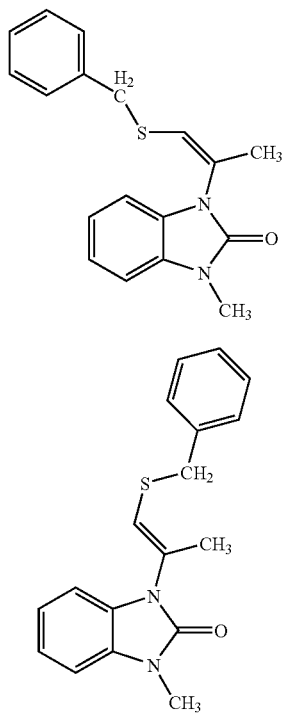

Stage A 3,9-dimethyl[1,3]thiazolo[3,2-a]benzimidazol-9-ium iodide The title compound is prepared as described in stage A of Example 1.

Stage B 167 mg of 3,9-dimethyl[1,3]thiazolo[3,2-a]benzimidazol-9-ium iodide (0.51 mmol) and 162 mg of NaOH (8 eq) were solubilised in benzyl alcohol (5 mL) and the solution stirred under reflux. After 48 h water was added (20 mL) and the mixture extracted with $CH_2Cl_2$ (3×20 mL). The organic layer was dried with $MgSO_4$ and evaporated under reduced pressure. The residue was then purified by chromatography on silica gel (eluent: $CH_2Cl_2$) to afford a mixture 55/45 of 1-[(1E)-1-(benzylsulfanyl)prop-1-en-2-yl]-3-methyl-1,3-dihydro-2H-benzimidazol-2-one and 1-[(1Z)-1-(benzyl sulfanyl)prop-1-en-2-yl]-3-methyl-1,3-dihydro-2H-benzimidazol-2-one isomers as a colourless oil (127 mg, 81% overall yield). HRMS m/z calcd $C_{18}H_{19}N_2OS$ [M+H]$^+$: 311.1212; found: 311.1215 (analysis on the isomer mixture). The two isomers were separated by preparative TLC (eluent: $CHCl_3$, eluted three times).

1-[(1E)-1-(benzyl sulfanyl)prop-1-en-2-yl]-3-methyl-1,3-dihydro-2H-benzimidazol-2-one: Rf=0.46 ($CHCl_3$); obtained as a colourless oil (46 mg, 36% yield), $^1$H NMR (300 MHz, $CDCl_3$) $\delta_H$ 2.13 (3H, d, J=0.8, $CH_3$), 3.39 (3H, s, $NCH_3$), 3.95 (2H, s, $SCH_2$), 6.16 (1H, q, J=0.8, H5), 6.64-7.10 (4H, m, arom), 7.25-7.36 (5H, m, arom); $^{13}$C NMR (75 MHz, $CDCl_3$) $\delta_C$ 16.98, 26.98, 38.04, 107.36, 108.54, 121.22, 121.44, 124.26, 127.34, 128.38, 128.70 (2C), 128.89 (2C), 129.07, 130.00, 137.60, 152.98.

1-[(1Z)-1-(benzylsulfanyl)prop-1-en-2-yl]-3-methyl-1,3-dihydro-2H-benzimidazol-2-one: Rf=0.34 ($CHCl_3$); obtained as a colourless oil (30 mg, 27% yield), $^1$H NMR (300 MHz, $CDCl_3$) $\delta_H$ 2.09 (3H, d, J=1.2, $CH_3$), 3.43 (3H, s, $NCH_3$), 3.84 (2H, s, $SCH_2$), 6.21 (1H, q, J=1.2, H5), 6.71-7.14 (4H, m, arom), 7.25-7.36 (5H, m, arom); $^{13}$C NMR (75 MHz, $CDCl_3$) $\delta_C$ 20.46, 27.10, 37.73, 107.51, 109.04, 121.13, 121.45, 124.61, 127.30, 127.40, 127.82, 128.58 (2C), 128.90 (2C), 130.29, 137.32, 152.42.

Example 4

Preparation of 1-benzyl-3-[(1Z)-1-(benzylsulfanyl)prop-1-en-2-yl]-1,3-dihydro-2H-benzimidazol-2-one and 1-benzyl-3-[(1E)-1-(benzylsulfanyl)prop-1-en-2-yl]-1,3-dihydro-2H-benzimidazol-2-one (III and III', R1=R2=Benzyl, R3=Me, R4=H)

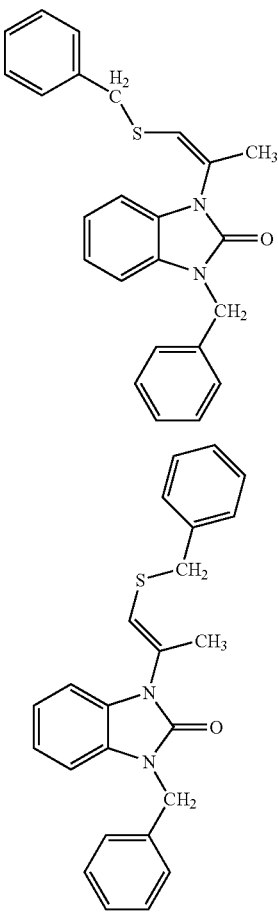

Stage A 9-benzyl-3-methyl[1,3]thiazolo[3,2-a]benzimidazol-9-ium chloride

The title compound is prepared as described in stage A of Example 2.

Stage B 200 mg of 9-benzyl-3-methyl[1,3]thiazolo[3,2-a]benzimidazol-9-ium chloride (0.32 mmol) and 204 mg of NaOH (8 eq) were solubilised in benzyl alcohol (5 mL) and the solution stirred under reflux. After 48 h water was added (20 mL) and the mixture extracted with $CH_2Cl_2$ (3×20 mL). The organic layer was dried with $MgSO_4$ and evaporated under reduced pressure. The residue containing 1-benzyl-3-[(1Z)-1-(benzylsulfanyl)prop-1-en-2-yl]-1,3-dihydro-2H-benzimidazol-2-one and 1-benzyl-3-[(1E)-1-(benzylsulfanyl)prop-1-en-2-yl]-1,3-dihydro-2H-benzimidazol-2-one isomers in 55/45 ratio was then purified (174 mg, 71% overall yield) and the isomer separated by preparative TLC (eluent: $CH_2Cl_2$, eluted four times). HRMS m/z calcd $C_{24}H_{23}N_2OS$ $[M+H]^+$: 387.1525; found: 387.1521 (analysis on the isomer mixture).

1-benzyl-3-[(1E)-1-(benzylsulfanyl)prop-1-en-2-yl]-1,3-dihydro-2H-benzimidazol-2-one: Rf=0.18 ($CH_2Cl_2$); obtained as a colourless oil (50 mg, 20% yield) $^1$H NMR (300 MHz, $CDCl_3$) $\delta_H$ 2.17 (3H, d, J=0.9, $CH_3$), 3.96 (2H, s, $SCH_2$), 5.04 (2H, s, $NCH_2$), 6.22 (1H, q, J=0.9, H5), 6.60-7.10 (4H, m, arom), 7.20-7.40 (10H, m, arom); $^{13}$C NMR (75 MHz, $CDCl_3$) $\delta_C$ 17.03, 38.06, 44.80, 108.25, 108.70, 121.34, 121.47, 124.39, 127.37, 127.56 (2C), 127.69, 128.25, 128.72 (2C), 128.73 (2C), 128.91 (2C), 129.19, 129.22, 136.14, 137.63, 152.97.

1-benzyl-3-[(1Z)-1-(benzylsulfanyl)prop-1-en-2-yl]-1,3-dihydro-2H-benzimidazol-2-one: Rf=0.10 ($CH_2Cl_2$); obtained as a colourless oil (64 mg, 26% yield) $^1$H NMR (300 MHz, $CDCl_3$) $\delta_H$ 2.14 (3H, d, J=1.2, $CH_3$), 3.86 (2H, s, $SCH_2$), 5.09 (2H, s, $NCH_2$), 6.25 (1H, q, J=1.2, H5), 6.70-7.10 (4H, m, arom), 7.20-7.40 (10H, m, arom); $^{13}$C NMR (75 MHz, $CDCl_3$) $\delta_C$ 20.54, 37.74, 44.78, 108.44, 109.12, 121.23, 121.45, 124.69, 127.31, 127.38 (2C), 127.57, 127.59, 127.95, 128.59 (2C), 128.69 (2C), 128.92 (2C), 129.44, 136.21, 137.34, 152.40.

Example 5

Preparation of 1-ethyl-3-[(1Z)-1-(methylsulfanyl)prop-1-en-2-yl]-1,3-dihydro-2H-benzimidazol-2-one (III: $R_1$=Et, $R_2$=$R_3$=Me, R4=H)

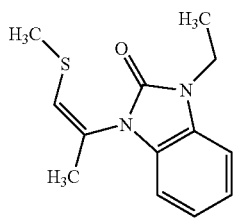

Stage A Preparation of 9-ethyl-3-methyl[1,3]thiazolo[3,2-a]benzimidazol-9-ium iodide

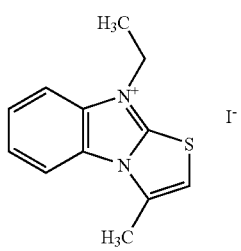

153 mg of 3-methyl[1,3]thiazolo[3,2-a]benzimidazole were solubilised in acetone (5 mL). Then 328 μl, (5 eq) of iodoethane were added and the solution stirred under reflux. After 18 h, 9-ethyl-3-methyl[1,3]thiazolo[3,2-a]benzimidazol-9-ium iodide was recovered as a white powder (267 mg, 96%) by filtration. Mp 268° C.; $^1$H NMR (300 MHz, MeOD) $\delta$=1.64 (3H, t, J=7.3, $CH_3$), 2.95 (3H, d, J=$CH_3$), 4.66 (2H, q, J=7.3, $CH_2$), 7.37 (1H, q, J=1.3, H5), 7.66-7.81 (2H, m, Ar), 8.01-8.04 (1H, m, Ar), 8.27-8.30 (1H, m, Ar); $^{13}$C NMR (75 MHz, MeOD) $\delta$=13.21, 14.25, 43.61, 112.19, 113.66, 114.93, 126.26, 128.32, 129.05, 135.29, 137.28, 155.62.

Stage B: 184 mg of 9-ethyl-3-methyl[1,3]thiazolo[3,2-a]benzimidazol-9-ium iodide (0.533 mmol) were solubilised in methanol (35 mL), then 231 mg (8 eq) of NaOMe were added and the solution stirred at room temperature. After 48 h the solvent was evaporated, water was added (20 mL) and the mixture extracted with $CH_2Cl_2$ (3×20 mL). The organic layer was dried with $MgSO_4$ and evaporated under reduced pressure to afford 1-ethyl-3-[(1Z)-1-(methylsulfanyl)prop-1-en-2-yl]-1,3-dihydro-2H-benzimidazol-2-one as a white powder (87 mg, 65%). Mp 74° C.; Rf=0.48 ($CH_2Cl_2$/AcOEt 8:2); $^1$H NMR (300 MHz, $CDCl_3$) $\delta$=1.35 (3H, t, J=7.2, $CH_3$), 2.13 (3H, d, J=1.1, $CH_3$), 2.22 (3H, s, $SCH_3$), 3.94 (2H, q, J=7.2, $CH_2$), 6.22 (1H, q, J=1.1, H5), 6.86 (1H, m, Ar), 6.99-7.09 (3H, m, Ar); $^{13}$C NMR (75 MHz, $CDCl_3$) $\delta$=13.46, 16.76, 20.28, 35.74, 107.58, 108.92, 120.81, 121.26, 126.59, 127.30, 127.50, 129.24, 151.75; HRMS m/z $C_{13}H_{17}N_2OS$ $[M+H]^+$ calcd: 249.1056, found: 249.1056.

Example 6

Preparation of 1-[3,5-bis(trifluoromethyl)benzyl]-3-[(1Z)-1-(methylsulfanyl)prop-1-en-2-yl]-1,3-dihydro-2H-benzimidazol-2-one (III: $R_1$=3,5-bis(trifluoromethyl)benzyl, $R_2$=$R_3$=Me, R4=H))

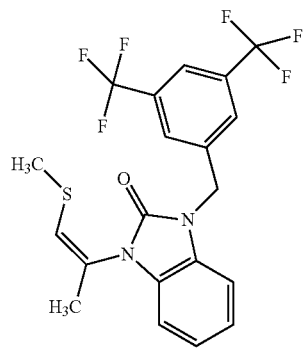

Stage A: Preparation of 9-[3,5-bis(trifluoromethyl)benzyl]-3-methyl[1,3]thiazolo[3,2-a]benzimidazol-9-ium chloride

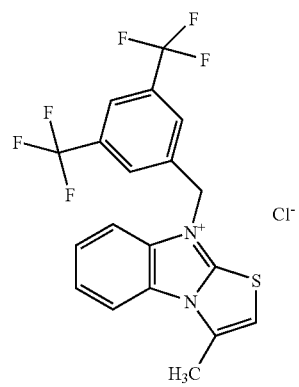

198 mg of 3-methyl[1,3]thiazolo[3,2-a]benzimidazole were solubilised in acetonitrile (2 mL). Then 828 mg (3 eq) of 3,5-bis(trifluoromethyl)benzyl chloride were added and the solution stirred under reflux. After 18 h, 9-[3,5-bis(trifluoromethyl)benzyl]-3-methyl[1,3]thiazolo[3,2-a]benzimidazol-9-ium chloride was recovered as a white powder (422 mg, 89%) by filtration. Mp>268° C.; $^1$H NMR (300 MHz, MeOD) δ=2.95 (3H, d, J=1.3, CH$_3$), 6.03 (2H, s, CH$_2$), 7.30 (1H, q, J=1.3, H5), 7.70-7.83 (2H, m, Ar), 8.02-8.04 (1H, m, Ar), 8.11 (1H, brs, Ar), 8.21 (2H, brs, Ar), 8.31-8.34 (1H, m, Ar); $^{13}$C NMR (75 MHz, MeOD) δ=14.11, 50.33, 112.73, 113.72, 115.13, 124.43 (1C, sept, J=4), 124.46 (2C, q, J=272), 126.67, 128.66, 129.20, 130.92 (2C, q, J=3), 133.72 (2C, q, J=34), 135.48, 136.62, 137.71, 156.38; HRMS m/z C$_{19}$H$_{13}$F$_6$N$_2$S [M−Cl]$^+$ calcd: 415.0698, found: 415.0698.

Stage B: 285 mg of 9-[3,5-bis(trifluoromethyl)benzyl]-3-methyl[1,3]thiazolo[3,2-a]benzimidazol-9-ium chloride (0.632 mmol) were solubilised in methanol (40 mL), then 274 mg (8 eq) of NaOMe were added and the solution stirred at room temperature. After 48 h the solvent was evaporated, water was added (20 mL) and the mixture extracted with CH$_2$Cl$_2$ (3×20 mL). The organic layer was dried with MgSO$_4$ and evaporated under reduced pressure to afford 1-[3,5-bis(trifluoromethyl)benzyl]-3-[(1Z)-1-(methylsulfanyl)prop-1-en-2-yl]-1,3-dihydro-2H-benzimidazol-2-one as a white powder (211 mg, 77%). Mp 148° C.; Rf=0.72 (CH$_2$Cl$_2$/AcOEt 8:2); $^1$H NMR (300 MHz, CDCl$_3$) δ=2.18 (3H, d, J=1.1, CH$_3$), 2.26 (3H, s, SCH$_3$), 5.20 (2H, brs, CH$_2$), 6.31 (1H, q, J=1.1, H5), 6.82-7.15 (4H, m, Ar), 7.75 (3H, brs, Ar); $^{13}$C NMR (75 MHz, CDCl$_3$) δ=16.79, 20.45, 43.95, 107.84, 109.41, 121.88, 121.88 (1C, sept, J=3), 122.00, 123.07 (2C, q, J=272), 126.34, 127.50 (2C, q, J=3), 127.94, 128.36, 128.78, 132.17 (2C, q, J=34), 139.07, 152.19; HRMS m/z C$_{20}$H$_{17}$F$_6$N$_2$OS [M+H]$^+$ calcd: 447.0960, found: 447.0959.

Example 7

Preparation of 1-heptyl-3-[(1Z)-1-(methylsulfanyl)prop-1-en-2-yl]-1,3-dihydro-2H-benzimidazol-2-one (III: R$_1$=heptyl, R$_2$=R$_3$=Me, R4=H)

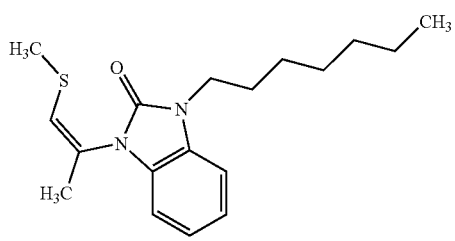

Stage A: Preparation of 9-heptyl-3-methyl[1,3]thiazolo[3,2-a]benzimidazol-9-ium iodide.

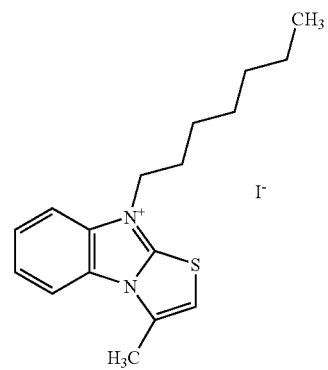

198 mg of 3-methyl[1,3]thiazolo[3,2-a]benzimidazole were added to 1-iodoheptane (3 mL). Then the mixture was stirred under reflux. After 18 h, 9-heptyl-3-methyl[1,3]thiazolo[3,2-a]benzimidazol-9-ium iodide was recovered as a pale green powder (421 mg, 97%) by filtration. Mp 137° C.; $^1$H NMR (300 MHz, MeOD) δ=0.8-0.91 (3H, m, CH$_3$), 1.22-1.54 (8H, m, 4-CH$_2$), 2.05 (2H, quint, J=7.4, CH$_2$), 2.95 (3H, d, J=1.3, CH$_3$), 4.60 (2H, t, J=7.2, CH$_2$), 7.36 (1H, q, J=1.3, H5), 7.64-7.82 (2H, m, Ar), 7.99-8.05 (1H, m, Ar), 8.26-8.32 (1H, m, Ar); $^{13}$C NMR (75 MHz, MeOD) δ=14.26, 14.35, 23.57, 27.71, 28.92, 29.89, 32.75, 48.48, 112.18, 113.78, 114.97, 126.30, 128.36, 129.01, 135.35, 137.63, 155.92; HRMS m/z C$_{17}$H$_{23}$N$_2$S [M−I]$^+$ calcd: 287.1576, found: 287.1576.

Stage B: 257 mg of 9-heptyl-3-methyl[1,3]thiazolo[3,2-a]benzimidazol-9-ium iodide (0.620 mmol) were solubilised in methanol (40 mL), then 268 mg (8 eq) of NaOMe were added and the solution stirred at room temperature. After 48 h the solvent was evaporated, water was added (20 mL) and the mixture extracted with CH$_2$Cl$_2$ (3×20 mL). The organic layer was dried with MgSO$_4$ and evaporated under reduced pressure to afford 1-heptyl-3-[(1Z)-1-(methylsulfanyl)prop-1-en-2-yl]-1,3-dihydro-2H-benzimidazol-2-one as a pale green oil (164 mg, 83%). Rf=0.65 (CH$_2$Cl$_2$/AcOEt 8:2); $^1$H NMR (300 MHz, CDCl$_3$) δ=0.82-0.87 (3H, m, CH$_3$), 1.14-1.44 (8H, m, 4-CH$_2$), 1.75 (2H, quint, J=7.1, CH$_2$), 2.12 (3H, d, J=1.2, CH$_3$), 2.21 (3H, s, SCH$_3$), 3.86 (2H, t, J=7.3, CH$_2$), 6.21 (1H, q, J=1.2, H5), 6.80-7.14 (4H, m, Ar). $^{13}$C NMR (75 MHz, CDCl$_3$) δ=13.86, 16.67, 20.20, 22.34, 26.52, 28.07, 28.70, 31.49, 40.91, 107.64, 108.80, 120.69, 121.15, 126.53, 127.23, 127.39, 129.52, 151.96; HRMS m/z C$_{18}$H$_{27}$N$_2$OS [M+H]$^+$ calcd: 319.1839, found: 319.1838.

Example 8

Preparation of 1-[(1Z)-1-(methylsulfanyl)prop-1-en-2-yl]-3-(4-nitrobenzyl)-1,3-dihydro-2H-benzimidazol-2-one. (III: R$_1$=4-nitrobenzyl, R$_2$=R$_3$=Me, R4=H)

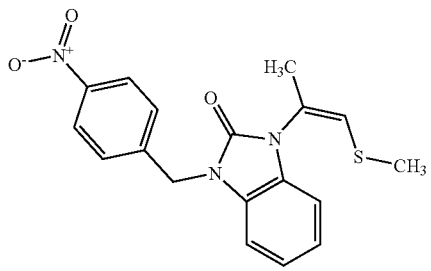

Stage A: Preparation of 3-methyl-9-(4-nitrobenzyl)[1,3]thiazolo[3,2-a]benzimidazol-9-ium chloride

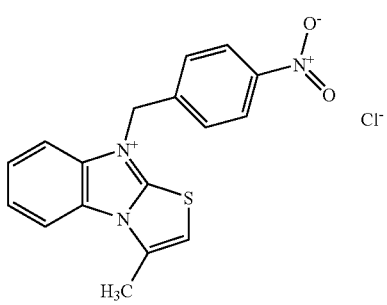

204 mg of 3-methyl[1,3]thiazolo[3,2-a]benzimidazole were solubilised in acetone (3 mL). Then 558 mg (3 eq) of 4-nitrobenzyl chloride were added and the solution stirred under reflux. After 18 h, 3-methyl-9-(4-nitrobenzyl)[1,3]thiazolo[3,2-a]benzimidazol-9-ium chloride was recovered as a pale yellow powder (363 mg, 94%) by filtration. Mp 241° C.; $^1$H NMR (300 MHz, MeOD) δ=2.95 (3H, d, J=1.3, CH$_3$), 5.97 (2H, s, CH$_2$), 7.30 (1H, q, J=1.3, H5), 7.68-7.82 (4H, m, Ar), 7.96-8.03 (1H, m, Ar), 8.27-8.36 (3H, m, Ar); $^{13}$C NMR (75 MHz, MeOD) δ=14.11, 50.56, 112.76, 113.82, 115.08, 125.37 (2C), 126.63, 128.64, 129.12, 131.04 (2C), 135.43, 137.72, 140.44, 149.92, 156.37; HRMS m/z C$_{17}$H$_{14}$N$_3$O$_2$S [M−Cl]$^−$ calcd: 324.0801, found: 324.0802.

Stage B: 163 mg of 3-methyl-9-(4-nitrobenzyl)[1,3]thiazolo[3,2-a]benzimidazol-9-ium chloride (0.450 mmol) were solubilised in methanol (30 mL), then 122 mg (5 eq) of NaOMe were added and the solution stirred at room temperature. After 48 h the solvent was evaporated, water was added (20 mL) and the mixture extracted with CH$_2$Cl$_2$ (3×20 mL). The organic layer was dried with MgSO$_4$ and evaporated under reduced pressure to afford 1-[(1Z)-1-(methylsulfanyl) prop-1-en-2-yl]-3-(4-nitrobenzyl)-1,3-dihydro-2H-benzimidazol-2-one as a pale yellow oil (140 mg, 91%). Rf=0.59 (CH$_2$Cl$_2$/AcOEt 8:2); $^1$H NMR (300 MHz, CDCl$_3$) δ=2.18 (3H, d, J=1.1, CH$_3$), 2.27 (3H, s, SCH$_3$), 5.19 (2H, brs, CH$_2$), 6.29 (1H, q, J=1.1, H5), 6.77-6.85 (1H, m, Ar), 6.88-6.96 (1H, m, Ar), 6.98-7.14 (2H, m, Ar), 7.42-7.52 (2H, m, Ar), 8.12-8.23 (4H, m, Ar); $^{13}$C NMR (75 MHz, CDCl$_3$) δ=16.88, 20.40, 44.09, 108.04, 109.35, 121.75, 121.82, 124.02 (2C), 126.23, 127.74, 128.03 (2C), 128.15, 128.90, 143.60, 147.48, 152.12; HRMS m/z C$_{18}$H$_{18}$N$_3$O$_3$S [M+H]$^+$ calcd: 356.1063, found: 356.1067.

Example 9

Preparation of 1-methyl-3-[(1Z)-1-(methylsulfanyl) prop-1-en-2-yl]-5-(trifluoromethyl)-1,3-dihydro-2H-benzimidazol-2-one (III: R$_1$=Me, R$_2$=R$_3$=Me, R4=5-CF3)

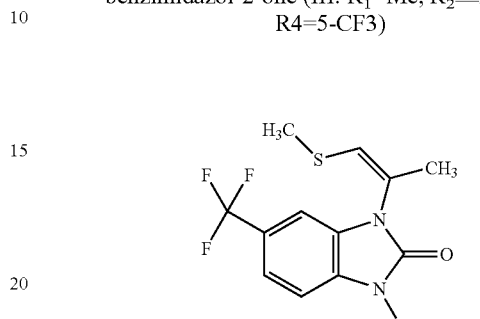

Stage A: Preparation of 3-[2-amino-5-(trifluoromethyl)phenyl]-4-methyl-1,3-thiazole-2(3H)-thione.

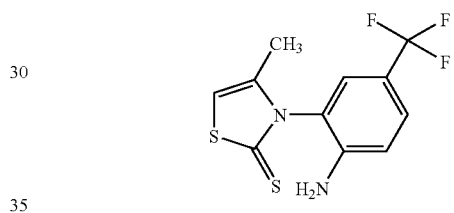

The title compound was prepared according to the following scheme:

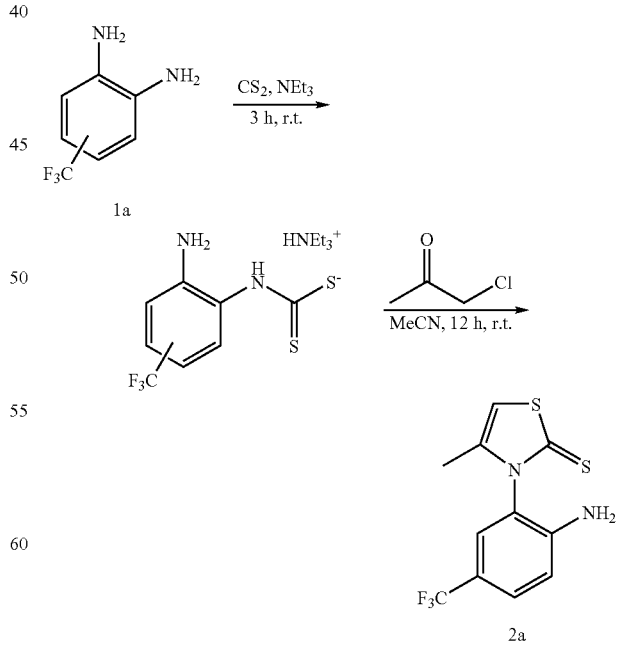

3 g of commercially available 1,2-diamino-4-trifluoromethylbenzene (1a) (17.03 mmol) were suspended in CS$_2$ (40 mL), then NEt₃ (2 eq, 5 mL) was added dropwise and the mixture stirred at r.t. for 3 h. The resulting dithiocarbamate salt (5.98 g, yellow powder, 99%) was filtered off, washed with Et₂O and used without further purification.

5.98 g of dithiocarbamate salt (16.92 mmol) were suspended in MeCN (50 mL), then commercially available 1-chloro-propan-2-one was added dropwise (1 eq, 1.36 mL) and the mixture stirred at r.t. for 12 h. The solvent was then removed and HCl 37% (4 mL) was added and the mixture vigorously stirred for 15 min. Water (200 mL) was added and the mixture extracted with 3×200 mL of CH₂Cl₂. The organic layer was then washed with 3×400 mL of water, dried over MgSO₄ and evaporated under reduced pressure. The resulting solid was then crystallised from EtOH to yield 2a 3-[2-amino-5-(trifluoromethyl)phenyl]-4-methyl-1,3-thiazole-2(3H)-thione as pale yellow crystals (3.32 g, 68%). Mp 188° C.; Rf=0.61 (CH₂Cl₂/AcOEt 9:1); ¹H NMR (200 MHz, CDCl₃) δ=1.95 (3H, d, J=1.12, CH₃), 4.04 (2H, brs, NH₂), 6.39 (1H, q, J=1.2, H5), 6.91-6.99 (1H, m, Ar), 7.27-7.31 (1H, m, Ar), 7.47-7.58 (1H, m, Ar); ¹³C NMR (75 MHz, CDCl₃) δ=15.53, 107.00, 117.18, 121.31 (q, J=34), 122.69, 123.96 (q, J=271), 126.41 (q, J=4), 127.98 (q, J=4), 132.60, 146.90, 172.15; HRMS m/z C₁₁H₉N₂F₃S₂ [M+H]⁺ calcd: 291.0231, found: 291.0231. The structure of 3-[2-amino-5-(trifluoromethyl)phenyl]-4-methyl-1,3-thiazole-2(3H)-thione was fully established by X-ray single crystal analysis.

Stage B: Preparation of 3-methyl-6-(trifluoromethyl)[1,3]thiazolo[3,2-a]benzimidazol-9-ium iodide (4a)

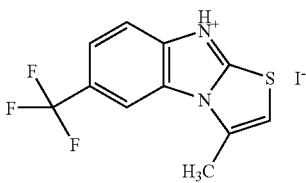

The title compound was prepared according to the following scheme

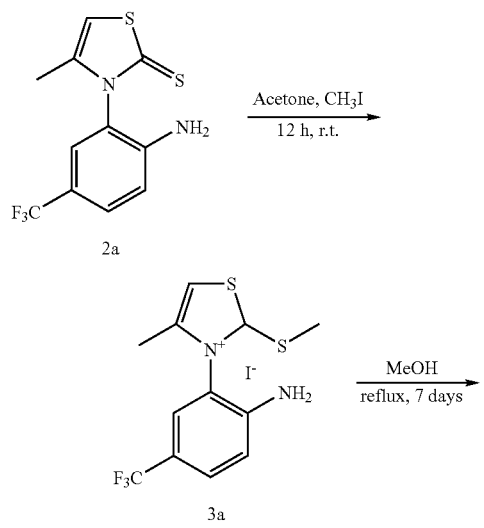

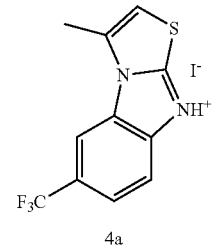

4a

Stage B1: Preparation of (3a) 3-[2-amino-5-(trifluoromethyl)phenyl]-4-methyl-2-(methylsulfanyl)-1,3-thiazol-3-ium iodide 1.34 g (4.61 mmol) of 3-[2-amino-5-(trifluoromethyl)phenyl]-4-methyl-1,3-thiazole-2(3H)-thione were solubilised in acetone (25 mL), then CH₃I (10 eq, 2.87 mL) was added and the solution stirred at r.t. for 12 h. 3-[2-amino-5-(trifluoromethyl)phenyl]-4-methyl-2-(methylsulfanyl)-1,3-thiazol-3-ium iodide (3a) was recovered by filtration (white powder, 1.19 g, 60%) and by evaporation of the organic layer (776 mg, 39%). Mp 194° C.; ¹H NMR (300 MHz, CD₃OD) δ=2.27 (3H, d, J=1.1, CH₃), 2.96 (3H, s, SCH₃), 7.10-7.18 (1H, m, Ar), 7.62-7.70 (2H, m, Ar), 7.86 (1H, q, J=1.1, H5); ¹³C NMR (75 MHz, CD₃OD) δ=13.74, 18.11, 118.28, 118.36, 118.68, 119.97 (q, J=34), 125.41 (q, J=270), 126.91 (q, J=4), 130.92 (q, J=4), 149.97, 148.73, 182.40; HRMS m/z C₁₂H₁₂N₂F₃S₂ [M−I]⁺ calcd: 305.0388, found: 305.0389.

Stage B2: (4a) 3-methyl-6-(trifluoromethyl)[1,3]thiazolo[3,2-a]benzimidazol-9-ium iodide:

1.1 g (2.54 mmol) of 3-[2-amino-5-(trifluoromethyl)phenyl]-4-methyl-2-(methylsulfanyl)-1,3-thiazol-3-ium iodide (3a) were solubilised in MeOH (100 mL) and the solution refluxed for 7 days. Then MeOH was evaporated to yield 3-methyl-6-(trifluoromethyl)[1,3]thiazolo[3,2-a]benzimidazol-9-ium iodide (4a) (orange powder, 970 mg, 99%). Mp 122° C.; ¹H NMR (300 MHz, CD₃OD) δ=2.80 (3H, d, J=1.3, CH₃), 6.88 (1H, q, J=1.3, H5), 7.65-7.71 (1H, m, Ar), 7.78-7.84 (1H, m, Ar), 8.17-8.22 (1H, m, Ar); ¹³C NMR (75 MHz, CD₃OD) δ=14.12, 108.58, 110.25 (q, J=4), 119.02, 121.99 (q, J=4), 124.52 (q, J=33), 126.07 (q, J=271), 130.34, 132.58, 149.35, 161.08; HRMS m/z C₁₁H₈N₂F₃S [M−I]⁺ calcd: 257.0355, found: 257.0353.

Stages B1 et B2 can be combined without isolation of 3-[2-amino-5-(trifluoromethyl)phenyl]-4-methyl-2-(methylsulfanyl)-1,3-thiazol-3-ium iodide (3a).

Stage C: preparation of 3-methyl-6-(trifluoromethyl)[1,3]thiazolo[3,2-a]benzimidazole 5a 1.4 g (3.64 mmol) of 3-methyl-6-(trifluoromethyl)[1,3]thiazolo[3,2-a]benzimidazol-9-ium iodide 4a were poured in a NaHCO₃ saturated aqueous solution (60 mL). The mixture was extracted 3×60 mL of CH₂Cl₂; the organic layer was dried with MgSO₄ and evaporated under reduced pressure to yield 3-methyl-6-(trifluoromethyl)[1,3]thiazolo[3,2-a]benzimidazole 5a (790 mg, yellow powder, 85%). Mp=127° C.; ¹H NMR (300 MHz, CDCl₃) δ=2.79 (3H, d, J=1.3, CH₃), 6.46 (1H, q, J=1.3, H5), 7.60-8.08 (3H, m, Ar); ¹³C NMR (75 MHz, CDCl₃) δ=14.44, 105.89, 108.10 (q, J=4), 119.39, 120.29 (q, J=4), 122.73 (q, J=32), 124.74 (q, J=272), 129.49, 129.87, 150.41, 159.70; HRMS m/z C₁₁H₇F₃N₂S [M+H]⁺ calcd: 257.0355, found: 257.0353. Same result as for (4a) 3-methyl-6-(trifluoromethyl)[1,3]thiazolo[3,2-a]benzimidazol-9-ium iodide.

Stage D: preparation of 3,9-dimethyl-6-(trifluoromethyl)[1,3]thiazolo[3,2-a][3,1]benzimidazol-9-ium iodide

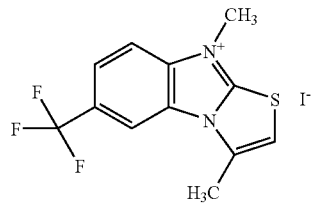

375 mg (1.46 mmol) of 3-methyl-6-(trifluoromethyl)[1,3]thiazolo[3,2-a]benzimidazole 5a were solubilised in acetone (15 mL), then CH$_3$I (10 eq, 0.9 mL) was added and the solution stirred at r.t. for 12 h. 3,9-dimethyl-6-(trifluoromethyl)[1,3]thiazolo[3,2-a][3,1]benzimidazol-9-ium iodide 6a was recovered by evaporation of the solvent (orange powder, 570 mg, 98%). Mp=>270° C.; $^1$H NMR (300 MHz, DMSO-d$_6$) δ=2.94 (3H, d, J=1.2, CH$_3$), 4.18 (3H, s, NH$_3$), 7.51 (1H, q, J=1.2, H5), 8.13-8.17 (1H, m, Ar), 8.28-8.21 (1H, m, Ar), 8.52-8.56 (1H, m, Ar); $^{13}$C NMR (75 MHz, DMSO-d$_6$) δ=13.44, 33.35, 111.68 (q, J=4), 112.76, 113.98, 123.59 (q, J=4), 123.95 (q, J=272), 124.08 (q, J=33), 126.48, 133.42, 138.76, 157.50; HRMS m/z C$_{12}$H$_{10}$F$_3$N$_2$S [M−I]$^+$ calcd: 271.0511, found: 271.0513.

Stage E 90 mg (0.23 mmol) of 3,9-dimethyl-6-(trifluoromethyl)[1,3]thiazolo[3,2-a][3,1]benzimidazol-9-ium iodide 6a were solubilised in MeOH (20 mL). NaOMe was added (8 eq, 100 mg) and the solution stirred under reflux for 2 h. The solvent was then evaporated and water was added (15 mL). The resulting mixture was extracted 3×15 mL of CH$_2$Cl$_2$, the organic layer dried with MgSO$_4$ and evaporated under reduced pressure to yield 1-methyl-3-[(1Z)-1-(methylsulfanyl)prop-1-en-2-yl]-5-(trifluoromethyl)-1,3-dihydro-2H-benzimidazol-2-one 7a (58 mg, orange oil, 85%). $^1$H NMR (300 MHz, CDCl$_3$) δ=2.14 (3H, d, J=1.2, CH$_3$), 2.27 (3H, s, SCH$_3$), 3.47 (3H, s, NCH$_3$), 6.29 (1H, q, J=1.2, H5), 7.03-7.10 (2H, m, Ar), 7.38-7.42 (1H, m, Ar); $^{13}$C NMR (75 MHz, CDCl$_3$) δ=16.90, 20.33, 27.36, 106.06 (q, J=4), 107.28, 119.02 (q, J=4), 123.69 (q, J=33), 124.55 (q, J=271), 125.83, 127.36, 128.53, 132.82, 152.50; HRMS m/z C$_{13}$H$_{14}$F$_3$N$_2$OS [M+H]$^+$ calcd: 303.0773, found: 303.0775.

Example 10

Preparation of 5-fluoro-3-methyl-1-[(1Z)-1-(methylsulfanyl)prop-1-en-2-yl]-1,3-dihydro-2H-benzimidazol-2-one (III: R$_1$=R$_2$=R3=Me, R$_4$=5-F)

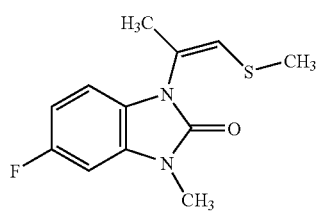

Stage A: Preparation of 3-(2-amino-4-fluorophenyl)-4-methyl-1,3-thiazole-2(3H)-thione (2b)

The title compound was prepared according to the following scheme

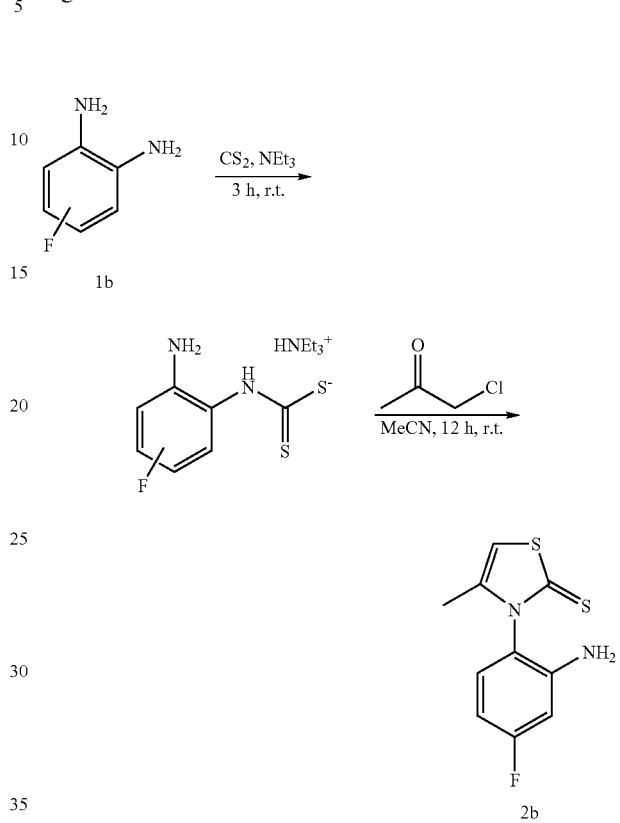

10 g (79 mmol) of commercially available 1,2-diamino-4-fluorobenzene 1b were suspended in CS$_2$ (500 mL), then NEt$_3$ (2 eq, 22 ml) were added dropwise and the mixture stirred at r.t. for 2 h. The resulting dithiocarbamate salt was then filtered off, washed with Et$_2$O and used without further purifications (24 g, yellow powder, 99%). 24 g (79 mmol) of dithiocarbamate salt were suspended in MeCN (500 mL), then commercially available chloroacetone (1.1 eq, 7.14 mL) was added dropwise and the mixture stirred at r.t. for 12 h. The solvent was then removed and HCl 37% (21 mL) was added under vigorous stirring. After 15 min, water (150 mL) was added and the mixture extracted 3×150 mL of CH$_2$Cl$_2$. The organic layer was washed 3×400 mL of water, dried with MgSO$_4$ and evaporated under reduced pressure. 3-(2-Amino-4-fluorophenyl)-4-methyl-1,3-thiazole-2(3H)-thione 2b was obtained by crystallisation from CH$_2$Cl$_2$ as yellow crystals (12.1 g, 68%). Mp=138° C.; $^1$H NMR (300 MHz, CDCl$_3$) δ=1.95 (3H, d, J=1.2, CH$_3$), 3.80 (2H, brs, NH$_2$), 6.37 (1H, q, J=1.2, H5), 6.57-6.99 (3H, m, Ar); $^{13}$C NMR (75 MHz, CDCl$_3$) δ=15.44, 103.9 (d, J=26), 106.4 (d, J=24), 106.6, 119.3 (d, J=3), 130.0 (d, J=11), 144.6 (d, J=12), 163.8 (d, J=248), 189.2; HRMS m/z C$_{10}$H$_{10}$N$_2$FS$_2$ [M+H]$^+$ calcd: 241.0264, found: 241.0262. The structure of 3-(2-amino-4-fluorophenyl)-4-methyl-1,3-thiazole-2(3H)-thione was fully established by X-ray single crystal analysis.

Stage B: Preparation of 7-fluoro-3-methyl[1,3]thiazolo[3,2-a]benzimidazol-9-ium iodide (4b)

The title compound was prepared according to the following scheme

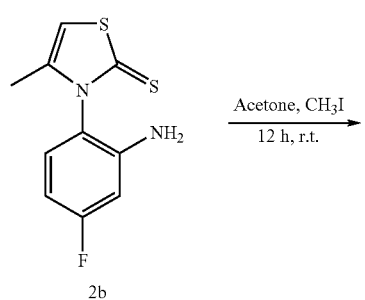

2b

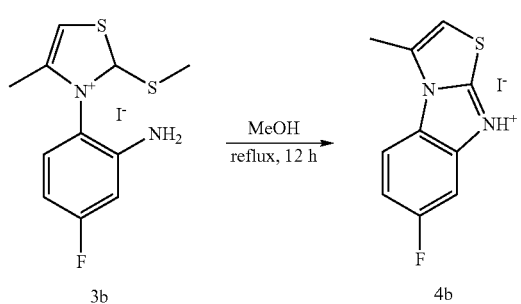

3b → 4b

Stage B1: Preparation of 3-(2-amino-4-fluorophenyl)-4-methyl-2-(methylsulfanyl)-1,3-thiazol-3-ium iodide (3b)

3 g (12.5 mmol) of 3-(2-amino-4-fluorophenyl)-4-methyl-1,3-thiazole-2(3H)-thione 2b obtained in stage A were solubilised in acetone (100 mL), then $CH_3I$ (10 eq, 7.8 mL) was added and the solution stirred at r.t. for 12 h. 3-(2-Amino-4-fluorophenyl)-4-methyl-2-(methylsulfanyl)-1,3-thiazol-3-ium iodide (3b) was recovered by filtration (pale yellow powder, 4.7 g, 98%). Mp=206° C.; $^1$H NMR (300 MHz, $CD_3OD$) δ=2.26 (3H, d, J=1.1, $CH_3$), 2.94 (3H, s, $SCH_3$), 6.51-7.27 (3H, m, Ar), 7.82 (1H, q, J=1.1, H5); $^{13}$C NMR (75 MHz, $CD_3OD$) δ=13.79, 17.97, 104.17 (d, J=27), 105.83 (d, J=25), 115.66 (d, J=2), 117.98, 130.83 (d, J=12), 147.65 (d, J=1), 148.28, 166.95 (d, J=248), 182.41; HRMS m/z $C_{11}H_{12}N_2FS_2$ [M−I]$^+$ calcd: 255.0420, found: 255.0417.

Stage B2: 2 g (5.23 mmol) of 3-(2-amino-4-fluorophenyl)-4-methyl-2-(methylsulfanyl)-1,3-thiazol-3-ium iodide obtained in stage B1 were solubilised in MeOH (200 mL) and the solution refluxed for 12 h. Then MeOH was evaporated to yield 7-fluoro-3-methyl[1,3]thiazolo[3,2-a]benzimidazol-9-ium iodide (4b) (pale yellow powder, 1.74 g, 99%). Mp=240° C.; $^1$H NMR (300 MHz, $CD_3OD$) δ=2.83 (3H, d, 0.1=1.3, $CH_3$), 7.03 (1H, q, J=1.3, H5), 7.20-7.27 (1H, m, Ar), 7.47-7.51 (1H, m, Ar), 8.06-8.11 (1H, m, Ar); $^{13}$C NMR (75 MHz, $CD_3OD$) δ=14.1, 103.5 (d, J=27), 109.9, 112.1 (d, J=27), 114.0 (d, J=10), 126.9, 133.3, 143.6 (d, J=10), 158.3, 162.0 (d, J=242); HRMS m/z $C_{10}H_8N_2FS$ [M−I]$^+$ calcd: 207.0387, found: 207.0388.

Stage C: Preparation of 7-fluoro-3,9-dimethyl[1,3]thiazolo[3,2-a]benzimidazol-9-ium iodide

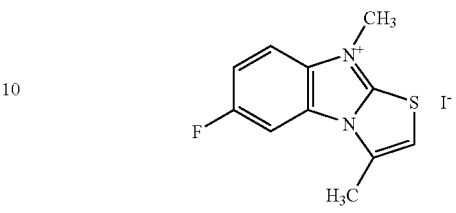

1 g (2.99 mmol) of 7-fluoro-3-methyl[1,3]thiazolo[3,2-a]benzimidazol-9-ium iodide obtained in stage B2 was poured in a $NaHCO_3$ saturated aqueous solution (50 mL). The mixture was extracted 3×50 mL of $CH_2Cl_2$; the organic layer was dried with $MgSO_4$ and evaporated under reduced pressure to yield 7-fluoro-3-methyl[1,3]thiazolo[3,2-a]benzimidazole (465 mg, yellow powder, 75%). Mp=148° C.; $^1$H NMR (300 MHz, $CDCl_3$) δ=2.68 (3H, d, J=0.8, $CH_3$), 6.34 (1H, q, J=0.8, H5), 6.91-7.66 (3H, in, Ar); $^{13}$C NMR (75 MHz, $CDCl_3$) δ=14.3, 104.8, 104.9 (d, J=23), 108.7 (d, J=26), 110.6 (d, J=10), 126.9, 129.7, 149.0 (d, J=12), 158.5, 159.6 (d, J=239); HRMS m/z $C_{10}H_8N_2FS$ [M+H]$^+$ calcd: 207.0387, found: 207.0386 400 mg (1.94 mmol) of 7-fluoro-3-methyl[1,3]thiazolo[3,2-a]benzimidazole were solubilised in acetone (10 mL), then $CH_3I$ (10 eq, 1.2 mL) was added and the solution stirred at r.t. for 12 h. 7-Fluoro-3-methyl[1,3]thiazolo[3,2-a]benzimidazol-9-ium iodide was recovered by filtration (white powder, 641 mg, 95%). Mp=>270° C.; $^1$H NMR (300 MHz, DMSO-$d_6$) δ=2.86 (3H, d, J=1.3, $CH_3$), 4.09 (3H, s, $NCH_3$), 7.46 (1H, q, J=1.3, H5), 7.51-7.58 (1H, in, Ar), 8.09-8.12 (1H, m, Ar), 8.28-8.33 (1H, m, Ar); $^{13}$C NMR (75 MHz, DMSO-$d_6$) δ=13.43, 33.22, 100.23 (d, J=29), 112.25, 112.51 (d, J=26), 115.47 (d, J=10), 126.67 (d, J=1), 133.02, 137.37 (d, J=14), 156.10, 160.45 (d, J=244); HRMS m/z $C_{11}H_{10}N_2FS$ [M−I]$^+$ calcd: 221.0543, found: 221.0546.

Stage D: 172 mg (0.49 mmol) of 7-fluoro-3-methyl[1,3]thiazolo[3,2-a]benzimidazol-9-ium iodide obtained in stage C were solubilised in MeOH (20 mL). NaOMe was added (4 eq, 107 mg) and the solution stirred at r.t. for 48 h. The solvent was then evaporated and water was added (10 mL). The resulting mixture was extracted 3×10 mL of $CH_2Cl_2$, the organic layer dried with $MgSO_4$ and evaporated under reduced pressure to yield 5-fluoro-3-methyl-1-[(1Z)-1-(methylsulfanyl)prop-1-en-2-yl]-1,3-dihydro-2H-benzimidazol-2-one.

(100 mg, white powder, 80%). Mp=110° C.; $^1$H NMR (300 MHz, $CDCl_3$) δ=2.11 (3H, d, J=1.1, $CH_3$), 2.25 (3H, s, $SCH_3$), 3.40 (3H, s, $NCH_3$), 6.23 (1H, q, J=1.1, H5), 6.68-6.84 (3H, m, Ar); $^{13}$C NMR (75 MHz, $CDCl_3$) δ=16.88, 20.29, 27.29, 96.05 (d, J=29), 107.41 (d, J=24), 109.18 (d, J=10), 123.44 (d, J=1.2), 126.39, 127.76, 130.92 (d, J=12), 152.65, 158.85 (d, J=238); HRMS m/z $C_{12}H_{14}N_2OFS$ [M+H]$^+$ calcd: 253.0805, found: 253.0803.

Example 11

Preparation of 1-benzyl-1,3-dihydro-2H-benzimidazol-2-one by hydrolysis of 1 benzyl-3-[(1Z)-1-(methylsulfanyl)prop-1-en-2-yl]-1,3-dihydro-2H-benzimidazol-2-one

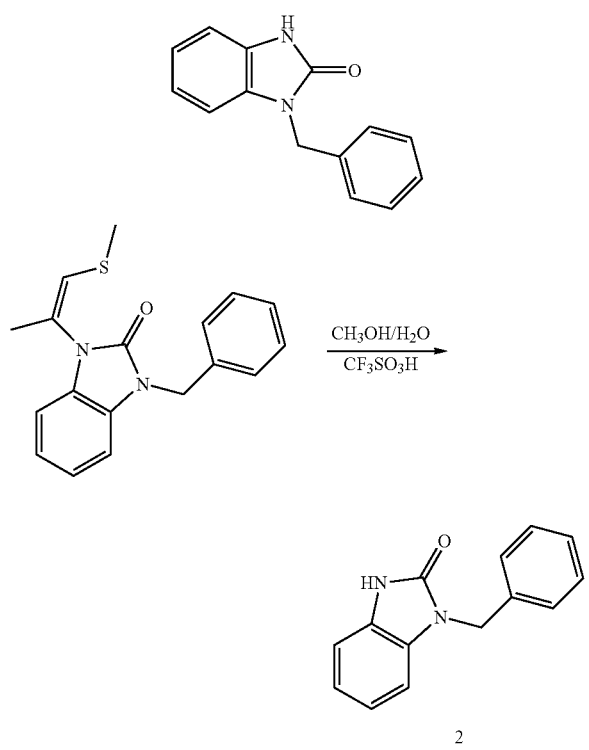

35 mg of 1-benzyl-3-[(1Z)-1-(methylsulfanyl)prop-1-en-2-yl]-1,3-dihydro-2H-benzimidazol-2-one 1 (0.113 mmol) prepared as described in example 2 were solubilised in a solution of MeOH/H$_2$O 1:1 (2 mL). Then, CF$_3$SO$_3$H (2 mL) was added and the solution refluxed under magnetic stirring. After 3 h, H$_2$O was added (5 mL) and the solution was extracted 3×10 mL of CH$_2$Cl$_2$. The resulting solid was finally chromatographed on silica gel (CH$_2$Cl$_2$/AcOEt 8:2) to yield 1-benzyl-1,3-dihydro-2H-benzimidazol-2-one 2 as a white powder (12 mg, 48%). Mp 194° C. (litt. G. Vernin, H. Domlog, C. Siv, J. Metzger, *J. Heterocyclic Chem.*, 18, 85 (1981): 198° C.); Rf=0.23 (CH$_2$Cl$_2$/AcOEt 8:2); $^1$H NMR (200 MHz, CDCl$_3$) δ=5.11 (2H, s, CH$_2$), 6.84-7.35 (9H, m, Ar), 10.08 (1H, brs, NH).

Example 12

Compounds with R$_1$ being a (substituted) benzyl group in compounds III and III' (examples 2, 4, 6 and 8) were studied in an In vitro Biological tests performed through a well established protocol using a BACE1 FRET assay Kit, Red developed by PanVera corporation Madison Wis. USA and marketed by Sigma-Aldrich. Each test was performed in duplicate. These compounds showed an IC$_{50}$ at 50+/−10 μM.

The invention claimed is:

1. Process for the preparation of a compound of formula (III) or (III') or a mixture thereof comprising the step of treating compound (II) with an alkoxide of formula R$_2$OM where M is a sodium or a potassium cation in the corresponding alcohol of formula R$_2$OH and wherein R$_1$ and R$_2$ being identical or different represent:

a linear or branched C$_1$-C$_{10}$ alkyl group optionally functionalized by
  one or more linear or cyclic C$_1$-C$_8$ O-alkyl or S-alkyl groups, and/or
  O-aryl having from 6 to 10 carbon atoms optionally substituted by one or more substitutes selected from the group consisting of a halogen, NO$_2$, CN, CF$_3$, CCl$_3$ and CO$_2$R$_i$;

an arylalkyl group consisting of an aromatic ring having from 6 to 10 carbon atoms optionally substituted by one or more substitutes selected from the group consisting of linear and branched C$_1$-C$_{10}$ alkyl, C$_1$-C$_4$ alkoxy, C$_6$-C$_{10}$-aryloxy groups, OH and CO$_2$R$_i$, linked to the sulfur heteroatom or nitrogen by a C$_1$-C$_4$ alkyl group; or A heterocyclic group, linked to the nitrogen or the sulfur heteroatom by an alkyl C$_1$-C$_4$ chain, optionally functionalized by one or several substituents selected from the group consisting of NO$_2$, CN, CF$_3$, CCl$_3$, a halogen, OH and CO$_2$R$_i$;

R$_3$ represents:
a linear or branched C$_1$-C$_{10}$ alkyl group optionally functionalized by C$_1$-C$_4$ alkoxy, C$_6$-C$_{10}$-aryloxy groups or halogen; or
a C$_6$-C$_{10}$ aryl or heterocyclic group optionally functionalized by one or several substituents selected from the group consisting of NO$_2$, CN, CF$_3$, CCl$_3$, a halogen, linear and branched C$_1$-C$_{10}$ alkyl, C$_1$-C$_4$ alkoxy, C$_6$-C$_{10}$-aryloxy groups, OH and CO$_2$R$_i$; and R4, wherein R4 can occupy any of the four positions of the aromatic ring and is selected from the group consisting of hydrogen, NO$_2$, CN, CF$_3$, CCl$_3$, a halogen, linear and branched C$_1$-C$_{10}$ alkyl, C$_1$-C$_4$ alkoxy, C$_6$-C$_{10}$-aryloxy groups, OH, and CO$_2$R$_i$ or wherein R$_4$ consists of one to four identical or different substituents selected from the group consisting of NO$_2$, CN, CF$_3$, CCl$_3$, a halogen, linear and branched $C_1$-$C_{10}$ alkyl, $C_1$-$C_4$ alkoxy, $C_6$-$C_{10}$-aryloxy groups, OH and $CO_2R_i$;
wherein $R_i$ is a $C_1$-$C_4$ alkyl group.

2. A process according to claim 1 wherein $R_2$ is Me, $R_3$ is Me, $R_4$ is H and $R_1$ is Me, Et, $C_3$-$C_{10}$ n-alkyl group, —$CH_2CH_2Oalkyl$, —$CH_2CH_2OCF_3$, —$CH_2CH_2(OCH_2CH_2)_n$—OH, —$CH_2CH_2$—$(OCH_2CH_2)_n$OMe, —$CH_2CH_2$—$(OCH_2CH_2)_n$OPh, —$CH_2CH_2$—$(SCH_2CH_2)_n$—OH, —$CH_2CH_2(SCH_2CH_2)_n$SMe, —$CH_2CH_2(SCH_2CH_2)_n$SPh, —$CH_2CH(OMe)_2$, —$CH_2CH(SMe)_2$, —$CH_2CH(O(CH_2)_n O)$, —$CH_2CH(S(CH_2)_n S)$, —$CH_2CH_2(OCH_2CH_2)_n$OPhR, or —$CH_2CH_2(OCH_2CH_2)_n$OPhRR', and wherein R and R' are identical or different and are each selected from the group consisting of o, m, p- $C_1$-$C_4$ alkyl, F, Cl, Br, I, $NO_2$, $CF_3$, $CCl_3$, CN and $CO_2Me$ and wherein n is 0 to 4.

3. A process according to claim 1 wherein $R_2$ is Me, $R_3$ is Me, $R_4$ is H and $R_1$ is benzyl, $CH_2PhR$ or $CH_2PhRR'$, wherein R and R' are identical or different and are each selected from the group consisting of o, m, p- $C_1$-$C_4$ alkyl, F, Cl, Br, I, $NO_2$, $CF_3$, $CCl_3$, CN and $CO_2Me$, or $R_1$ is $CH_2Ar$ in which Ar is 2-naphthalenyl or 1-naphthalenyl optionally functionalized by F, Cl, Br, I, $NO_2$, $CF_3$, $CCl_3$, CN or $CO_2Me$.

4. A process according to claim 3 wherein $R_2$ is benzyl.

5. A process according to claim 1 wherein $R_1$ is Me, $R_3$ is Me, $R_4$ is H and $R_2$ is benzyl, $CH_2PhR$ or $CH_2PhRR'$, wherein R and R' are identical or different and are each selected from the group consisting of o, m, p- $C_1$-$C_4$ alkyl, F, Cl, Br, I, $NO_2$, $CF_3$, $CCl_3$, CN and $CO_2Me$, or $R_2$ is $CH_2$-Heterocycle in which Heterocycle is 2-pyridyl, 3-pyridyl, 4-pyridyl, 2-thienyl, 3-thienyl, 2-furanyl, 3-furanyl, 2-thiazolyl, 2-benzothiazolyl, 2-imidazolyl or furfuryl, or $R_2$ is $CH_2Ar$ in which Ar is 2-naphthalenyl or 1-naphthalenyl optionally functionalized by F, Cl, Br, I, $NO_2$, $CF_3$, $CCl_3$, CN or $CO_2Me$.

6. A process according to claim 1 wherein $R_1$ is benzyl, $R_3$ is Me, $R_4$ is H and $R_2$ is benzyl, $CH_2PhR$ or $CH_2PhRR'$, wherein R and R' are identical or different and are each selected from the group consisting of o, m, p- $C_1$-$C_4$ alkyl, F, Cl, Br, I, $NO_2$, $CF_3$, $CCl_3$, CN and $CO_2Me$, or $R_2$ is $CH_2$-Heterocycle in which Heterocycle is 2-pyridyl, 3-pyridyl, 4-pyridyl, 2-thienyl, 3-thienyl, 2-furanyl, 3-furanyl, 2-thiazolyl, 2-benzothiazolyl, 2-imidazolyl or furfuryl.

7. A process according to claim 1 wherein $R_1$ is Me, $R_3$ is Me, $R_4$ is H and $R_2$ is Me, Et, $C_3$-$C_{10}$ n-alkyl group, —$CH_2CH_2Oalkyl$, —$CH_2CH_2OCF_3$, —$CH_2CH_2(OCH_2CH_2)_n$—OH, —$CH_2CH_2$—$(OCH_2CH_2)_n$OMe, —$CH_2CH_2$—$(OCH_2CH_2)_n$OPh, —$CH_2CH_2$—$(SCH_2CH_2)_n$—OH, —$CH_2CH_2(SCH_2CH_2)_n$SMe, —$CH_2CH_2(SCH_2CH_2)_n$SPh, —$CH_2CH(OMe)_2$, —$CH_2CH(SMe)_2$, —$CH_2CH(O(CH_2)_n O)$, —$CH_2CH(S(CH_2)_n S)$, —$CH_2CH_2(OCH_2CH_2)_n$OPhR, or —$CH_2CH_2(OCH_2CH_2)_n$OPhRR', and wherein R and R' identical or different and are each selected from the group consisting of o, m, p- $C_1$-$C_4$ alkyl, F, Cl, Br, I, $NO_2$, $CF_3$, $CCl_3$, CN and $CO_2Me$ and wherein n is 0 to 4.

8. A process according to claim 1 wherein $R_1$ is Me or benzyl, $R_2$ is Me or benzyl, $R_3$ is Me, R4 in position 4 or 5 is $CF_3$, F, Cl, Br, $NO_2$, CN, Me or MeO or $R_4$ is 4,5-dichloro, 4,5-dimethyl or 4,5-dimethoxy.

9. A process according to claim 1 for selectively obtaining a compound of formula (III) wherein the step of treating is conducted at a temperature below 60° C.

10. Process according to claim 1 for obtaining a mixture of a compound of formula (III) or (III') wherein the step of treating is conducted at a temperature above 70° C.

11. Process for obtaining compound (IV) comprising

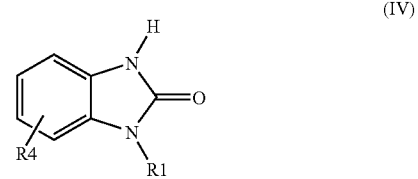

(IV)

hydrolyzing a compound of formula (III) or (III') as defined by claim 1 in a mixture MeOH and water; and
catalyzing the mixture with the compound of formula (III) or (III') with a protonic acid.

12. A compound of formula (III) or (III') or a mixture thereof,

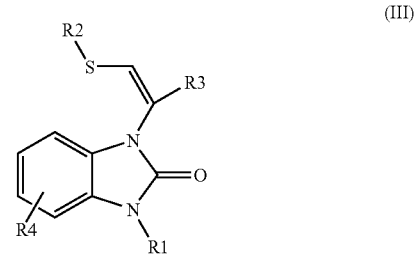

(III)

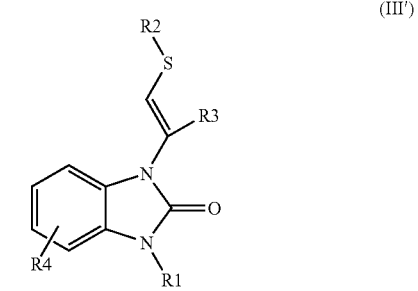

(III')

$R_1$, $R_2$, $R_3$ and $R_4$ being as defined in claim 1, or a pharmaceutical acceptable salt thereof.

13. A compound according to claim 12 selected from the group consisting of:

1-methyl-3-[(1Z)-1-(methylsulfanyl)prop-1-en-2-yl]-1,3-dihydro-2H-benzimidazol-2-one;
1-benzyl-3-[(1Z)-1-(methylsulfanyl)prop-1-en-2-yl]-1,3-dihydro-2H-benzimidazol-2-one);
1-[(1Z)-1-(benzylsulfanyl)prop-1-en-2-yl]-3-methyl-1,3-dihydro-2H-benzimidazol-2-one;
1-[(1E)-1-(benzylsulfanyl)prop-1-en-2-yl]-3-methyl-1,3-dihydro-2H-benzimidazol-2-one;
1-benzyl-3-[(1Z)-1-(benzylsulfanyl)prop-1-en-2-yl]-1,3-dihydro-2H-benzimidazol-2-one;
1-benzyl-3-[(1E)-1-(benzylsulfanyl)prop-1-en-2-yl]-1,3-dihydro-2H-benzimidazol-2-one;
1-ethyl-3-[(1Z)-1-(methylsulfanyl)prop-1-en-2-yl]-1,3-dihydro-2H-benzimidazol-2-one;
1-[3,5-bis(trifluoromethyl)benzyl]-3-[(1Z)-1-(methylsulfanyl)prop-1-en-2-yl]-1,3-dihydro-2H-benzimidazol-2-one;
1-heptyl-3-[(1Z)-1-(methylsulfanyl)prop-1-en-2-yl]-1,3-dihydro-2H-benzimidazol-2-one;
1-[(1Z)-1-(methylsulfanyl)prop-1-en-2-yl]-3-(4-nitrobenzyl)-1,3-dihydro-2H-benzimidazol-2-one;
1-methyl-3-[(1Z)-1-(methylsulfanyl)prop-1-en-2-yl]-5-(trifluoromethyl)-1,3-dihydro-2H-benzimidazol-2-one;

5-fluoro-3-methyl-1-[(1Z)-1-(methylsulfanyl)prop-1-en-2-yl]-1,3-dihydro-2H-benzimidazol-2-one;
or a pharmaceutical acceptable salt thereof.

14. A pharmaceutical composition comprising at least one compound according to claim 12 and a pharmacologically acceptable carrier.

15. A pharmaceutical composition comprising at least one compound according to claim 13 and a pharmacologically acceptable carrier.

16. A method of inhibiting BACE 1 comprising administering the pharmaceutical composition according to claim 14.

17. A method of inhibiting BACE 1 comprising administering the pharmaceutical composition according to claim 15.

18. A method for the treatment of Alzheimer disease in a human or other animal subject, comprising administering an effective amount of a compound of formula III or III' as defined in claim 12 to said subject.

19. A method for the treatment of Alzheimer disease in a human or other animal subject, comprising administering an effective amount of a compound of formula III or III' as defined in claim 13 to said subject 20. A process according to claim 1 for selectively obtaining compound (III) wherein the step of treating is conducted at a temperature from about 18 to 35° C.

21. Process according to claim 1 for obtaining a mixture of compound (III) and (III') wherein the step of treating is conducted at a temperature above 100° C.

* * * * *